US008728463B2

(12) United States Patent
Atala et al.

(10) Patent No.: US 8,728,463 B2
(45) Date of Patent: May 20, 2014

(54) PRODUCTION OF TISSUE ENGINEERED DIGITS AND LIMBS

(75) Inventors: Anthony Atala, Winston Salem, NC (US); James Yoo, Winstom Salem, NC (US); Grace Lim, Winston-Salem, NC (US); Sang Jin Lee, Winston-Salem, NC (US)

(73) Assignee: Wake Forest University Health Science, Winston-Salem, NC (US)

( * ) Notice: Subject to any disclaimer, the term of this patent is extended or adjusted under 35 U.S.C. 154(b) by 1090 days.

(21) Appl. No.: 11/373,046

(22) Filed: Mar. 10, 2006

(65) Prior Publication Data
US 2006/0257377 A1 Nov. 16, 2006

Related U.S. Application Data

(60) Provisional application No. 60/660,832, filed on Mar. 11, 2005, provisional application No. 60/663,458, filed on Mar. 18, 2005.

(51) Int. Cl.
*A01N 63/00* (2006.01)

(52) U.S. Cl.
USPC ...................................................... 424/93.7

(58) Field of Classification Search
None
See application file for complete search history.

(56) References Cited

U.S. PATENT DOCUMENTS

| 5,281,422 A * | 1/1994 | Badylak et al. ............ 623/13.11 |
| 5,645,532 A | 7/1997 | Horgan |
| 5,698,271 A | 12/1997 | Liberti et al. |
| 5,855,610 A * | 1/1999 | Vacanti et al. ............... 623/2.13 |
| 5,922,028 A * | 7/1999 | Plouhar et al. ............. 623/23.72 |
| 6,009,832 A | 1/2000 | Innings et al. |
| 6,143,293 A * | 11/2000 | Weiss et al. .................. 424/93.7 |
| 6,171,344 B1 * | 1/2001 | Atala ......................... 623/23.64 |
| 6,428,802 B1 * | 8/2002 | Atala ........................... 424/423 |
| 6,471,993 B1 | 10/2002 | Shastri et al. |
| 6,530,956 B1 | 3/2003 | Mansmann |
| 6,537,567 B1 | 3/2003 | Niklason et al. |
| 6,592,623 B1 | 7/2003 | Bowlin et al. |
| 6,596,296 B1 | 7/2003 | Nelson et al. |
| 6,649,159 B2 | 11/2003 | Yang et al. |
| 7,179,287 B2 | 2/2007 | Wolfinbarger, Jr. |
| 7,531,503 B2 | 5/2009 | Atala et al. |
| 7,622,299 B2 | 11/2009 | Sanders et al. |
| 2002/0028243 A1 | 3/2002 | Masters |
| 2002/0034476 A1 | 3/2002 | Lauffer et al. |
| 2002/0081732 A1 | 6/2002 | Bowlin et al. |
| 2002/0087174 A1 | 7/2002 | Capello |
| 2002/0090725 A1 | 7/2002 | Simpson et al. |
| 2003/0021821 A1 | 1/2003 | Fertala et al. |
| 2003/0097180 A1 * | 5/2003 | Tormala et al. ............ 623/13.18 |
| 2003/0219417 A1 | 11/2003 | Wolfinbarger |
| 2004/0005297 A1 | 1/2004 | Connelly et al. |
| 2004/0009600 A1 * | 1/2004 | Bowlin et al. ................. 435/395 |
| 2004/0044403 A1 | 3/2004 | Bischoff et al. |
| 2004/0093081 A1 * | 5/2004 | Nilsson et al. .............. 623/13.18 |
| 2004/0110439 A1 | 6/2004 | Chaikof et al. |
| 2004/0117033 A1 * | 6/2004 | Frondoza et al. ........... 623/23.72 |
| 2004/0146546 A1 | 7/2004 | Gravett et al. |
| 2004/0249464 A1 * | 12/2004 | Bindseil et al. ............. 623/17.16 |
| 2005/0095695 A1 | 5/2005 | Shindler et al. |
| 2005/0142161 A1 | 6/2005 | Freeman et al. |
| 2005/0266067 A1 | 12/2005 | Sengupta et al. |
| 2006/0204441 A1 | 9/2006 | Atala et al. |
| 2006/0204445 A1 | 9/2006 | Atala et al. |
| 2006/0204539 A1 | 9/2006 | Atala et al. |
| 2006/0240061 A1 | 10/2006 | Atala et al. |
| 2006/0246584 A1 | 11/2006 | Covelli |
| 2006/0253192 A1 | 11/2006 | Atala et al. |
| 2006/0257377 A1 | 11/2006 | Atala et al. |
| 2007/0213801 A1 | 9/2007 | Kutryk et al. |
| 2008/0003184 A1 | 1/2008 | Uvdal et al. |
| 2010/0129450 A1 | 5/2010 | Atala et al. |

FOREIGN PATENT DOCUMENTS

| DE | 2917037 B1 | 4/1980 |
| DE | 19919625 A1 | 11/2000 |
| DE | 20019928 U1 | 2/2001 |
| EP | 1 405 649 A1 | 4/2004 |
| EP | 1604697 A1 | 12/2005 |
| JP | 2004-162244 A | 6/2004 |
| WO | 9911191 A1 | 3/1999 |
| WO | WO 99/48541 | 9/1999 |
| WO | 0127365 A1 | 4/2001 |
| WO | WO 0137884 | 5/2001 |
| WO | 0180921 A2 | 11/2001 |
| WO | WO 02/00149 | 1/2002 |
| WO | 0230482 A1 | 4/2002 |
| WO | WO 03/007790 A2 | 1/2003 |

(Continued)

OTHER PUBLICATIONS

Ott, M. et al. "Sheer stress-conditioned, endothelial cell-seeded vascular grafts: Improved cell adherence in response to in vitro shear stress," *Surgery*, Mar. 1995, pp. 334-339.

Ballou et al., "Noninvasive Imaging of Quantum Dots in Mice", *Bioconjugate Chem.*, vol. 15, pp. 79-86, 2004.

Chen et al., "The Use of a PLGA Fiber/Collagen Composite Web As a Scaffold for Engineering of Articular Cartilage Tissue With Adjustable Thickness", *J. Biomed Mater Res A*, Dec. 15, 2003;67(4): 1170-80.

Hafemann et al., "Use of a Collagen/Elastin-Membrane for the Tissue Engineering of Dermis", *Burns*, vol. 25, pp. 373-384, 1999.

(Continued)

*Primary Examiner* — Suzanne Ziska

(74) *Attorney, Agent, or Firm* — Thomas J. Engellenner; Reza Mollaaghababa; Pepper Hamilton LLP

(57) ABSTRACT

The invention pertains to methods of producing artificial composite tissue constructs that permit coordinated motion. Biocompatible structural matrices having sufficient rigidity to provide structural support for cartilage-forming cells and bone-forming cells are used. Biocompatable flexible matrices seeded with muscle cells are joined to the structural matrices to produce artificial composite tissue constructs that are capable of coordinated motion.

30 Claims, 15 Drawing Sheets

(56) References Cited

FOREIGN PATENT DOCUMENTS

| WO | 04000915 A2 | 12/2003 |
|---|---|---|
| WO | WO 2004/014304 | 2/2004 |
| WO | WO 2004/044281 | 5/2004 |
| WO | 2004-045425 A1 | 6/2004 |
| WO | 2004098420 A2 | 11/2004 |
| WO | WO 2005/020849 A2 | 3/2005 |

OTHER PUBLICATIONS

Hirsch et al., "Nanoshell-Mediated Near-Infrared Thermal Therapy of Tumors Under Magnetic Resonance Guidance", *PNAS*, vol. 100, pp. 13549-13554, 2003.
Liao et al., "Hierarchically Biomimetic Bone Scaffold Materials: Nano-HA/Collagen/PLA Composite", *J. Biomed Mater Res B Appl Biomater* May 15, 2004;69(2): 158-65.
Klebe, R.J., "Cytoscribing: A Method for Micropositioning Cells and the Construction of Two- and three-Dimensional Synthetic Tissues", *Experimental Cell Research*, v. 179, pp. 362-373, 1988.
Huang, J Biomat Sci, Dec. 2001, pp. 979-993.
International Search Report and Written Opinion, PCT/US2006/008964, dated Feb. 5, 2007.
Magarey, Aust. J. Exp. Biol. Med. Sci., vol. 35, pp. 347-352, 1957.
Japanese Office Action Appl. JP2008-501058 dated Feb. 14, 2012. (8 pages).
Australian Search Report Appl. No. 2006223063 dated Oct. 19, 2010.
European Office Action Appl. 06738128.5 dated May 6, 2008.
European Office Action Appl. 06738128.5 dated Oct. 15, 2010.
Australian Office Action Appl. No. 2006223112 dated Sep. 30, 2010.
European Office Action Appl. 06738070.9 dated Sep. 4, 2008.
Japanese Office Action Appl. JP2008-501039 dated Apr. 5, 2011.
Gnasso, Atherosclerosis, 2001, 156:171-176.

\* cited by examiner

PRODUCTION OF TISSUE ENGINEERED DIGITS AND LIMBS

RELATED APPLICATIONS

The present application claims priority to U.S. Provisional Application Ser. No. 60/663,458, filed Mar. 18, 2005 and U.S. Provisional Application No. 60/660,832, filed Mar. 11, 2005, the contents of which are hereby incorporated by reference in their entirety.

BACKGROUND OF THE INVENTION

The technical field of this invention relates to artificial tissue constructs and method of creating such constructs.

Extremity injuries arising from battlefield trauma, which have become more prevalent in the past few years, have resulted in an amputation rate of approximately 29 percent. In addition to battlefield trauma, accidents caused by automobile collisions, falls, operation of machinery and heavy loading, also damage or break bones and can injure connective and interstitial tissues. Large limb amputation, as well as loss of fingers and toes leads to a significant impact on the standard of life for the patient. Finger amputations are particularly disabling due to the highly functional nature of the human hand and the day-to-day dependence on that functionality.

Conventional approaches to restore function to these patients have included whole hand transplants, prosthetics, as well as toe-to-finger and finger-to-thumb replantation. These techniques aim to restore hand function, and functional prehension by the restoration of an opposable digit, which is key to the patient's recovery. Unfortunately, these approaches have resulted in sub-optimal outcomes and limited functional restoration.

Accordingly, a need exists for alternative methods of replacing or repairing missing and damaged digits and limbs.

SUMMARY OF THE INVENTION

The present invention provides methods and compositions for preparing tissue engineered functional digits and limbs. This is accomplished by generating composite tissues (i.e., tissue containing bone, muscle, tendon, ligament, nerve, blood vessel), grown from cells isolated from the patient or a donor, that provide coordinated motion. In addition, "intelligent" scaffold systems are disclosed that support clinically relevant tissue dimensions and restoration of digit and limb function. This is particularly important for creating limbs because these intelligent scaffolds address the increased biological demands of engineering large tissues, especially in a perfusion deficient environment. These intelligent scaffold system are capable of releasing angiogenic and neurogenic factors to enhance tissue maturation and functionality. The diffusional limitations can be overcome by incorporation of vascular endothelial growth factor (VEGF) which enhances vascularisation in the muscle component of the composite tissue and also encourages recruitment of other cells. In addition, nerve growth can be stimulated by nerve growth factor (NGF), a potent axonal guiding mediator that promotes reinnervation of tissues.

The invention involves seeding multiple cell types on a scaffold matrix system that is capable of maturing into a composite tissue comprising a muscle-bone composite, or muscle-cartilage composite. The scaffold matrix system involves using a structural matrix having sufficient rigidity to provide structural support for bone and cartilage and a flexible matrix that is able to contract and relax with the muscle tissue formed thereon. The muscle tissue provides elasticity and contractability. The structural matrix and the flexible matrix are joined to create an artificial composite tissue construct capable of moving like native digits and limbs.

Accordingly, the invention pertains to a method of producing an artificial composite tissue construct permitting coordinated motion. The method involves using a first biocompatible structural matrix having sufficient rigidity to provide structural support, and seeding the first matrix with an isolated population of cells selected from the group consisting of cartilage-forming cells, bone-forming cells and combinations thereof. A second biocompatible flexible matrix is seeded with an isolated population of muscle progenitor cells (MPCs). The structural matrix and the flexible matrix are joined to produce an artificial composite tissue construct capable of coordinated motion.

More than one structural matrix can be used. Two separate structural matrices can be joined together by the flexible matrix to provide a flexible linkage between the two matrices. The tissue construct can be joined to the subject by joining the flexible matrix to the structural matrix and the natural bone structure.

The structural matrix can be an electrospun substrate, a decellularized substrate, or a synthetic polymer substrate with rigid properties, and the flexible matrix can be selected a decellularized submucosa substrate (e.g., a decellularized bladder submucosa) or an electrospun substrate.

The invention also discloses a biocompatible composite scaffolding system capable of providing structural support for engineered bone tissue comprising a biodegradable synthetic polymer and naturally derived collagen matrix. The biocompatible composite scaffolds of the present invention are non-toxic, easily fabricated and provide structural features that enhance the formation of bone tissue for therapeutic regeneration. The synthetic polymer can be selected from the group comprising poly(lactide-co-glycolide) (PLGA), poly (lactide) (PLA), poly(glycolic acid) (PGA), poly(caprolactone), polycarbonates, polyamides, polyanhydrides, polyamino acids, polyortho esters, polyacetals, polycyanoacrylates, degradable polyurethanes, hydroxyapatite (HA), tricalcium phosphate (TCP), and calcium sulfate. The naturally derived collagen matrix is submucosa, such as bladder submucosa (BSM). The composite scaffolding system can be fabricated using a solvent casting/particulate leaching process. The biocompatible composite scaffolding system preferably has a substantially uniform porous structures having an average pore diameter ranging from about 50 to about 250 μm, preferably from about 90 to about 150 μm, and most preferably from about 110 to about 130 μm. The porosity of the biocompatible composite scaffolding is greater than about 50%, preferably greater than about 80%, more preferably greater than about 90%, and most preferably greater than about 94%.

In another aspect, the invention provides a method of fabricating a biocompatible composite scaffolding system capable of providing structural support for regenerated bone tissue comprising selecting a pore size, obtaining porogens of the selected size, adding the porogens to a solution containing a synthetic polymer and submucosa and mixing to distribute the porogens and form a composite scaffold, drying the composite scaffold to remove residual solvent, and removing the porogens from the composite scaffold. The method can further include sieving porogens through a sieve to obtain the selected size porogens. The step of removing the porogens from the composite scaffold can comprise immersion in water.

Methods of joining the structural matrix and the flexible matrix include, but are not limited to, joining technique such as suturing, heating, and gluing with biological glue.

The structural matrix and the flexible matrix may further comprise a biological agent selected from the group consisting of nutrients, growth factors, cytokines, extracellular matrix components, inducers of differentiation, products of secretion, immunomodulators, proteins, antibodies, nucleic acids molecules, carbohydrates, and biologically-active compounds which enhance or allow growth of the cellular network or nerve fibers.

In one embodiment, the biological agent is a growth factor selected from the group consisting of transforming growth factor-alpha (TGF-α), transforming growth factor-beta (TGF-β), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor.

Examples of bone-forming cells that be seeded on the structural matrix include, but are not limited to, osteogenic cells, osteoblasts, osteocytes, osteoclasts, and bone-lining cells. Examples of cartilage-forming cells include, but are not limited to, chondrocytes and chondroblasts.

In another aspect, the invention pertains to a method for treating a subject with a limb or digit disorder. The method involves providing an artificial composite tissue construct having coordinated motion. The artificial composite tissue comprises a first biocompatable structural matrix having sufficient rigidity to provide structural support that is seeded with an isolated population of cells selected from the group consisting of cartilage-forming cells, bone-forming cells and combinations thereof, and a second biocompatable flexible matrix that is seeded with an isolated population of muscle progenitor cells (MPCs). The structural matrix and the flexible matrix are joined together such that the artificial composite tissue has coordinated motion. This artificial composite tissue is attached to a subject by joining the flexible matrix to the structural matrix and the natural bone structure of the subject such that there is a flexible linkage between the structural matrix and the bone structure. The improvement in the limb or digit disorder can then be monitored by measuring parameters such as mobility of the digit or limb, the extensor and flexor function, the motor function, the sensory function, the contractile response, and the tensile response.

In yet another aspect, the invention pertains to a muscle-cartilage composite construct or a muscle-bone composite construct made by the method of the invention.

DETAILED DESCRIPTION

Figure 1:
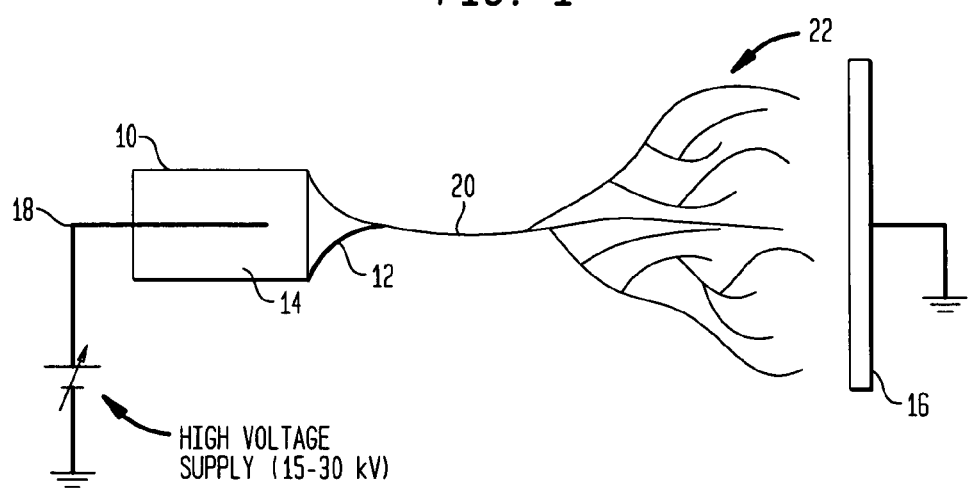
FIG. 1 is a schematic of an electrospin apparatus.

So that the invention may more readily be understood, certain terms are first defined:

The term "attach" or "attaches" as used herein refers to cells that adhere directly or indirectly to a substrate as well as to cells that adhere to other cells.

The phrase "biocompatible substrate" as used herein refers to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of an structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

The term "subject" as used herein is intended to include living organisms in which an immune response is elicited. Preferred subjects are mammals. Examples of subjects include but are not limited to, humans, monkeys, dogs, cats, mice, rats, cows, horses, pigs, goats and sheep.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra.

The phrase "three-dimensional scaffold" as used herein refers to the residual infra-structure formed when a natural biostructure, e.g. an organ, is decellularized. This complex, three-dimensional, scaffold provides the supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ. This three-dimensional scaffold can be perfused with a population of cultured cells, e.g., endothelial cells, which grow and develop to provide an endothelial tissue layer capable of supporting growth and development of at least one additional cultured cell population.

The term "natural biostructure" as used herein refers to a biological arrangement found within a subject, for example, organs, that include but are not limited, heart, kidney, liver, pancreas, spleen, bladder, ureter and urethra. The term "natural biostructure" is also intended to include parts of biostructures, for example parts of organs, for example, the renal artery of a kidney.

The terms "electrospinning" or "electrospun," as used herein with reference to electrospun materials refers to any method where materials are streamed, sprayed, sputtered, dripped, or otherwise transported in the presence of an electric field. The electrospun material can be deposited from the direction of a charged container towards a grounded target, or from a grounded container in the direction of a charged target. In particular, the term "electrospinning" means a process in which fibers are formed from a charged solution comprising at least one natural biological material, at least one synthetic polymer material, or a combination thereof by streaming the electrically charged solution through an opening or orifice towards a grounded target.

A natural biological material can be a naturally occurring organic material including any material naturally found in the body of a mammal, plant, or other organism. A synthetic polymer material can be any material prepared through a method of artificial synthesis, processing, or manufacture. Preferably the synthetic materials is a biologically compatible material. The natural or synthetic materials are also those that are capable of being charged under an electric field.

The terms "solution" and "fluid" as used herein describe a liquid that is capable of being charged and which comprises at least one natural material, at least one synthetic material, or a combination thereof. In a preferred embodiment, the fluid comprises at least one type of collagen, an additional natural material such as at least one type of elastin and at least one synthetic polymer, e.g., poly-L glycolic acid (PLGA).

The term "co-polymer" as used herein is intended to encompass co-polymers, ter-polymers, and higher order multiple polymer compositions formed by block, graph or random combination of polymeric components.

The term "intelligent scaffold" as used herein refers to a biocompatible substrate that is able to recruit cells, encourage cell growth and maturation, and facilitate the formation of a vascular support (e.g. blood vessels) and innervation (nerve formation) via controlled release of factors, such as vascular endothelial growth factor (VEGF) and nerve growth factor (NGF). The intelligent scaffold possesses the ultrastructural, biochemical and biological characteristics required for cell attachment, neovascularization, innervation and tissue maturation, even in an environment with a limited blood supply and is able to meet the metabolic demands of the growing cells.

The term "coordinated motion" as used herein refers to an artificial composite tissue construct that is made up of one or more structural matrices attached together by a flexible matrix such that to provide synchronized or harmonized movement and locomotion The coordinated motion mimics the motion of native digits and limbs. For example, a native finger or thumb is able to bend and flex, and likewise, the artificial composite tissue construct is able to bend and flex.

I. Limbs

In one aspect, the invention pertains to creating a tissue engineered digits and limbs. The limb system performs numerous tasks, including structural support and locomotion. It is composed of many tissues, including the bone, cartilage, tendon, muscle, nerve and blood vessels. Composite tissues that provide coordinated motion can be generated using multiple tissue types that are engineered to restore a portion of a digit.

In spite of the diversity of the form and function of various limbs, all limbs have substantial physiological similarities to each other. For example, limbs are typically composed of the same essential materials, regardless of specialized function or shape. A significant portion of the limb is composed of bone and muscle. Bone primarily has organic material, mostly protein-associated glycosaminoglycans and especially collagen, a protein commonly found in connective tissues and in extracellular matrixes. About half of the bone mass is mineral, and the most common bone-associated mineral is a calcium compound that closely resembles hydroxyapetite.

Bone typically has bone-producing cell types such as osteogenic cells, osteoblasts, and osteoclasts, for example. Another example of physiological similarities shared by various types of bones is vascularization. Blood vessels penetrate and permeate the bone through a series of channels and canals. These channels and canals can vary in location, length, and diameter. Examples of such channels include the canaliculi, haversian canals, osteons, Volkmann's canals, and others. These canals bring blood, nutrients, and other vital factors to and carry away waste from the multitude of cells that live in and that form the bone. One important example of such a bone-dwelling cell is the pluripotent stem cell that can differentiate into and form any of the cells of the blood or immune system. The blood and immune cells themselves also reside, at least for a time, in the bone. Such cells include macrophages, neutrophils, B cells, various T cells, eosinophils, basophils, megakaryocytes (the progenitor of platelets), and red blood cells. There are also varieties of bone-forming cells such as the osteoclasts, osteoblasts, and osteogenic cells mentioned above that live in the bone. Attached to the bones may be various tendons and other connective tissues that cooperate with the bones and any connected muscles to establish the articulation of movement or to secure tissues in place.

Yet another example of shared bone physiology is the specialized structures located at one or both ends of some bones. These specialized structures are adapted to hold a bone in a joint, while at the same time giving some degree of freedom and relative motion to the jointed bones. Examples of this type of arrangement include the bones that form the elbow, knee, shoulder, finger, ankle, foot, vertebral, and similarly movable joints. In addition to these and other physiological similarities, bones also can share developmental similarities. For example, the process of either intramembraneous ossification or endochondral ossification forms the bones, wherein the latter process involves a cartilaginous intermediate that is calcified to form the resulting bone tissue. Fibroblast cells typically lay down a network of collagen fibrils, upon which are deposited the calcium crystals in a mineral form approximating hydroxyapetite.

As can be understood by those skilled in the art, the complexity of bone functions and structures establish a skeletal system having significant capabilities. Bone tissue is not only a mechanical structure, but is also a complex and diverse combination of living, dynamic, and continuously regenerating tissues.

The anatomy of digits and limbs can readily be determined from for example, Gray's Anatomy, The Anatomical Basis of Medicine and Surgery, 39th Edition (2005). The methods and compositions of the invention are used for the reconstruction of artificial digits and limbs that mimic the native in vivo digit and limits structure. In particular, the invention pertains to generating digits and limbs of the hand. The hand contains three main groups of bones, the carpal bones, metacarpal bones, and the phalanges. Additionally, the hand also contains some small bony structures termed sesamoid bones. The carpel bones consist of the scaphoid, lunate, triquetrum, pisiform, trapezium, trapezoid, capitate, and hamate bones. The carpal bones join each other by planer-type joints. The carpal tunnel transmits the median nerve and the tendons The carpal bones joins to the metacarpal bones to form the carpometacarpal joint. The hand has five metacarpal bones. The first metacarpal bone constitutes the skeleton of the thumb. The other four metacarpal bones contact with the trapezoid, capitate and hamate, and lateral-medial surfaces of metacarpal bones. The heads of the metacarpal bones, which form the knuckles, articulate with the proximal phalanges. The hand has 14 phalanges. Each finger contains three phalanges, but each thumb only has two.

The hand also contains eight tendons of the flexor digitorum superficialis and profundus, the tendons of the flexor pollicis longus, and the flexor carpi radialis which pass throughout the carpal tunnel, and reach the carpal bones or fingers. Muscles of the hand occupy the space between the metacarpals, such as the abductor, oppenens, and flexor muscles. The hand also has a complex and rich vascular network provided by the radial and ulnar arteries.

In addition, the hand contains radial nerves that provides sensory feedback, median nerves that provide motor and sensitive innervation to the hand, and ulnar nerves, that has sensory and motor branches similar to the median nerve. The deep branch of the ulnar nerve innervates the muscles of the hand.

Although the hand is described in detail, the methods and compositions of the invention can be used to create any limb using the same methodology. The use of "intelligent scaffolds" further enhances the ability to create larger limbs because these scaffolds encourage the attraction of cells to the scaffold and also provide factors such as VEGF and NGF, that induce cell growth and innervation on the scaffold.

II. Electrospun Matrices

The invention pertains to methods and compositions for producing and using electrospun matrices. The process of electrospinning generally involves the creation of an electrical field at the surface of a liquid. The resulting electrical forces create a jet of liquid which carries electrical charge. The liquid jets may be attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening); or by a curing mechanism (chemically induced hardening). The produced fibers are collected on a suitably located, oppositely charged target substrate.

The electrospinning apparatus includes an electrodepositing mechanism and a target substrate. The electrodepositing mechanism includes at least one container to hold the solution that is to be electrospun. The container has at least one orifice or nozzle to allow the streaming of the solution from the container. If there are multiple containers, a plurality of nozzles may be used.

One or more pumps (e.g., a syringe pump) used in connection with the container can be used to control the flow of solution streaming from the container through the nozzle. The pump can be programmed to increase or decrease the flow at different points during electrospinning.

The electrospinning occurs due to the presence of a charge in either the orifices or the target, while the other is grounded. In some embodiments, the nozzle or orifice is charged and the target is grounded. Those of skill in the electrospinning arts will recognize that the nozzle and solution can be grounded and the target can be electrically charged.

The target can also be specifically charged or grounded along a preselected pattern so that the solution streamed from the orifice is directed into specific directions. The electric field can be controlled by a microprocessor to create an electrospun matrix having a desired geometry. The target and the nozzle or nozzles can be engineered to be movable with respect to each other thereby allowing additional control over the geometry of the electrospun matrix to be formed. The entire process can be controlled by a microprocessor that is programmed with specific parameters that will obtain a specific preselected electrospun matrix.

In embodiments in which two materials combine to form a third material, the solutions containing these components can be mixed together immediately before they are streamed from an orifice in the electrospinning procedure. In this way, the third material forms literally as the microfibers in the electrospinning process.

While the following is a description of a preferred method, other protocols can be followed to achieve the same result. In FIG. 1, a container 10, (e.g., a syringe or micropipette), with an orifice or nozzle 12 (e.g. a Taylor cone), is filled with a solution with at least one natural material, and at least one synthetic material 14. The container 10 is suspended opposite a grounded target 16, such as a metal ground screen. A fine wire 18 is placed in the solution to charge the solution in the container to a high voltage. At a specific voltage determined for each solution, the solution in the container nozzle is directed towards the grounded target. The single jet stream 20 of materials forms a splayed jet 22, upon reaching the grounded target, e.g., a rapidly rotating mandrel. The splayed jet collects and dries to form a three-dimensional, ultra thin, interconnected matrix of electrospun fibers. In some embodiments, a plurality of containers can be used with each of the containers holding a different compound.

Minimal electrical current is involved in the electrospinning process, therefore the process does not denature the materials that form the electrospun matrix, because the current causes little or no temperature increase in the solutions during the procedure.

The electrospinning process can be manipulated to meet the specific requirements for any given application of the electrospun matrix. In one embodiment, a syringe can be mounted on a frame that moves in the x, y and z planes with respect to the grounded substrate. In another embodiment, a syringe can be mounted around a grounded substrate, for instance a tubular mandrel. In this way, the materials that form the matrix streamed from the a syringe can be specifically aimed or patterned. Although the micropipette can be moved manually, the frame onto which the a syringe is mounted can also be controlled by a microprocessor and a motor that allows the pattern of streaming to be predetermined. Such microprocessors and motors are known to one of ordinary skill in the art, for example matrix fibers can be oriented in a specific direction, they can be layered, or they can be programmed to be completely random and not oriented.

The degree of branching can be varied by many factors including, but not limited to, voltage (for example ranging from about 0 to 30,000 volts), distance from a syringe tip to the substrate (for example from 1-100 cm, 0-40 cm, and 1-10 cm), the speed of rotation, the shape of the mandrel, the relative position of the a syringe tip and target (i.e. in front of, above, below, aside etc.), and the diameter of a syringe tip (approximately 0-2 mm), and the concentration and ratios of compounds that form the electrospun matrix. Other parameters which are important include those affecting evaporation of solvents such as temperature, pressure, humidity. The molecular weight of the polymer improves its ability to entangle and form fibers, and polymers with the molecular weight of 100 kDa generally performed. Those skilled in the art will recognize that these and other parameters can be varied to form electrospun materials with characteristics that are particularly adapted for specific applications.

The geometry of the grounded target can be modified to produce a desired matrix. By varying the ground geometry, for instance having a planar or linear or multiple points ground, the direction of the streaming materials can be varied and customized to a particular application. For instance, a grounded target comprising a series of parallel lines can be used to orient electrospun materials in a specific direction. The grounded target can be a cylindrical mandrel whereby a tubular matrix is formed. The ground can be variable surface that can be controlled by a microprocessor that dictates a specific ground geometry that is programmed into it. Alternatively, the ground can be mounted on a frame that moves in the x, y, and z planes with respect to a stationary container, e.g., a syringe or micropipette tip.

Electrospinning allows great flexibility and allows for customizing the construct to virtually any shape needed. In shaping matrices, portions of the matrix may be sealed to one another by, for example, heat sealing, chemical sealing, and application of mechanical pressure or a combination thereof. The electrospun compositions may be shaped into shapes such as a skin patch, an intraperitoneal implant, a subdermal implant, the interior lining of a stent, a cardiovascular valve, a tendon, a ligament, a muscle implant, a nerve guide and the like.

The electrospinning process can also be modified for example by (i) using mixed solutions (for example, materials along with substances such as cells, growth factors, or both) in the same container to produce fibers composed of electrospun compounds as well as one or more substances to produce a "blend," and (ii) applying agents such as Teflon onto the target to facilitate the removal of electrospun compounds from the target (i.e. make the matrix more slippery so that the electrospun matrix does not stick to the target).

The various properties of the electrospun materials can be adjusted in accordance with the needs and specifications of the cells to be suspended and grown within them. The porosity, for instance, can be varied in accordance with the method of making the electrospun materials or matrix. Electrospinning a particular matrix, for instance, can be varied by fiber size and density. If the cells to be grown in the matrix require a high nutrient flow and waste expulsion, then a loose matrix can be created. On the other hand, if the tissue to be made requires a dense environment, then a dense matrix can be designed. Porosity can be manipulated by mixing salts or other extractable agents. Removing the salt will leave holes of defined sizes in the matrix.

One embodiment for appropriate conditions for electrospinning a matrix is as follows. For electrospinning a matrix by combining 45% collagen I, 15% elastin and 40% PLGA, the appropriate approximate ranges are: voltage 0-30,000 volts (10-100 kV potential preferably 15-30 kV); pH 7.0 to 8.0; temperature 20 to 40° C., e.g., room temperature of 25° C.; and the distance from the container to the grounded plate can range from about 1 cm to about 100 cm, preferably about 1 cm to 10 cm. In addition to depositing the charged fibers on the grounded plate, the fibers can be deposited onto another substrate such as a stainless steel mandrel. The mandrel can be rotated at 20-1000 rpm, preferably about 300-700 rpm.

Examples of naturally occurring materials include, but are not limited to, amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans. In a preferred embodiment, the materials compound is an extracellular matrix material, including but not limited to collagen, fibrin, elastin, laminin, fibronectin, hyaluronic acid, chondroitin 4-sulfate, chondroitin 6-sulfate, dermatan sulfate, heparin sulfate, heparin, and keratan sulfate, and proteoglycans. These materials may be isolated from humans or other animals or cells. A preferred natural compound is collagen. Examples of collagen include, but are not limited to collagen I, collagen II, collagen III, collagen IV, collagen V, collagen VI, collagen VII, collagen VIII, collagen IX, and collagen X. Another preferred natural compound is elastin. Elastin fibers are responsible for the elastic properties of several tissues. Elastin is found, for example, in skin, blood vessels, and tissues of the lung where it imparts strength, elasticity and flexibility.

One class of synthetic polymer materials are biocompatible synthetic polymers. Such polymers include, but are not limited to, poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), poly-lactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO) and polyorthoesters or any other similar synthetic polymers that may be developed that are biologically compatible. A preferred synthetic polymer is PGLA.

In matrices composed of electrospun elastin (for elasticity), electrospun collagen (to promote cell infiltration and lend mechanical integrity), and other components, such as PLGA, PGA, PLA, PEO, PVA, or other blends, the relative ratio of the different components in the matrix can be tailored to specific applications (e.g. more elastin, less collagen depending on the tissue to be engineered).

Electrospun matrices can be formed of electrospun fibers of synthetic polymers that are biologically compatible. The term "biologically compatible" includes copolymers and blends, and any other combinations of the forgoing either together or with other polymers. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated herein by reference.

When both natural and synthetic materials are used in an electrospun matrix, the natural material component can range from about 5 percent to about 95 percent, preferably from about 25 percent to about 75 percent by weight. The synthetic material component can range from about 5 percent to about 95 percent, preferably from about 25 percent to about 75 percent by weight. In certain embodiments, both collagen and elastin can be included as natural material components, preferably with a predominance of collagen, e.g., greater than 40 percent of the natural material component. Ratios of collagen, elastin, and PLGA may be tailored to fit the application: for instances, normal levels of collagen and elastin vary from the more elastic vessels closer to the heart to less compliant vessels further from the heart. A vessel such as the aorta would have greater elastin content than a distal vessel. The percentages of collagen I, elastin, and other collagens (collagen III for blood vessels or collagen II, for instance, for cartilage) may be whatever is desired, as long as the molecular weight of these collagens is sufficient to form fibers in the electrospinning process. Ratios of collagen I may be from 40% to 80%, or 50%-100%. Elastin may also be used in higher ratios from 5% to 50%. PLGA or another synthetic biodegradable polymer may be used as desired in ratios from 5 to 80%. For a completely biological substrate, synthetic polymers may be omitted completely and only biological polymers may be used.

The compounds to be electrospun can be present in the solution at any concentration that will allow electrospinning. In one embodiment, the compounds may be electrospun are present in the solution at concentrations between 0 and about 1.000 g/ml. In another embodiment, the compounds to be electrospun are present in the solution at total solution concentrations between 10-15 w/v % (100-150 mg/ml or 0-0.1 g/L).

The compounds can be dissolved in any solvent that allows delivery of the compound to the orifice, tip of a syringe, under conditions that the compound is electrospun. Solvents useful for dissolving or suspending a material or a substance will depend on the compound. Electrospinning techniques often require more specific solvent conditions. For example, collagen can be electrodeposited as a solution or suspension in water, 2,2,2-trifluoroethanol, 1,1,1,3,3,3-hexafluoro-2-propanol (also known as hexafluoroisopropanol or HFIP), or combinations thereof. Fibrin monomer can be electrodeposited or electrospun from solvents such as urea, monochloroacetic acid, water, 2,2,2-trifluoroethanol, HFIP, or combinations thereof. Elastin can be electrodeposited as a solution or suspension in water, 2,2,2-trifluoroethanol, isopropanol, HFIP, or combinations thereof, such as isopropanol and water. In one desirable embodiment, elastin is electrospun from a solution of 70% isopropanol and 30% water containing 250 mg/ml of elastin. Other lower order alcohols, especially halogenated alcohols, may be used. Other solvents that may be used or combined with other solvents in electrospinning natural matrix materials include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone. Organic solvents such as methanol, chloroform, and trifluoroethanol (TFE) and emulsifying agents.

The selection of a solvent is based in part on consideration of secondary forces that stabilize polymer-polymer interactions and the solvent's ability to replace these with strong polymer-solvent interactions. In the case of polypeptides such as collagen, and in the absence of covalent crosslinking, the principal secondary forces between chains are: (1) coulombic, resulting from attraction of fixed charges on the backbone and dictated by the primary structure (e.g., lysine and arginine residues will be positively charged at physiological pH, while aspartic or glutamic acid residues will be negatively charged); (2) dipole-dipole, resulting from interactions of permanent dipoles; the hydrogen bond, commonly found in polypeptides, is the strongest of such interactions; and (3) hydrophobic interactions, resulting from association of nonpolar regions of the polypeptide due to a low tendency of non-polar species to interact favorably with polar water molecules. Therefore, solvents or solvent combinations that can favorably compete for these interactions can dissolve or disperse polypeptides. For example, HFIP and TFE possess a highly polar OH bond adjacent to a very hydrophobic fluorinated region. While not wanting to be bound by the following theories, it is believed that the alcohol portion can hydrogen bond with peptides, and can also solvate charges on the backbone, thus reducing Coulombic interactions between molecules. Additionally, the hydrophobic portions of these solvents can interact with hydrophobic domains in polypeptides, helping to resist the tendency of the latter to aggregate via hydrophobic interactions. It is further believed that solvents such as HFIP and TFE, due to their lower overall polarities compared to water, do not compete well for intramolecular hydrogen bonds that stabilize secondary structures such as an alpha helix. Consequently, alpha helices in these solvents are believed to be stabilized by virtue of stronger intramolecular hydrogen bonds. The stabilization of polypeptide secondary structures in these solvents is believed desirable, especially in the cases of collagen and elastin, to preserve the proper formation of collagen fibrils during electrospinning.

In one embodiment, the solvent has a relatively high vapor pressure to promote the stabilization of an electrospinning jet to create a fiber as the solvent evaporates. In embodiments involving higher boiling point solvents, it is often desirable to facilitate solvent evaporation by warming the spinning or spraying solution, and optionally the electrospinning stream itself, or by electrospinning in reduced atmospheric pressure. It is also believed that creation of a stable jet resulting in a fiber is facilitated by a high surface tension of the polymer/solvent mixture.

Similar to conventional electrospinning, midair electrospinning can be used which employs the same experimental set-up as other electrospinning techniques. However, in order to precipitate fibers before they reach the grounded target, the distance from the needle to the grounded target can be increased. For example, increasing the distance from the 10-30 cm to a distance of 30-40 cm. The field strength can be maintained or altered by increasing the applied potential at the needle tip. Increasing the distance from the needle tip to the grounded target allows the polymer jet to experience a longer "flight time." The added flight time, allows the solvent to be completely evaporated from the jet allowing the fibers to fully develop.

By varying the composition of the fibers being electrospun, it will be appreciated that fibers having different physical or chemical properties may be obtained. This can be accomplished either by spinning a liquid containing a plurality of components, each of which may contribute a desired characteristic to the finished product, or by simultaneously spinning fibers of different compositions from multiple liquid sources, that are then simultaneously deposited to form a matrix. The resulting matrix comprises layers of intermingled fibers of different compounds. This plurality of layers of different materials can convey a desired characteristic to the resulting composite matrix with each different layer providing a different property, for example one layer may contribute to elasticity while another layer contributes to the mechanical strength of the composite matrix. These methods can be used to create tissues with multiple layers such as blood vessels.

The electrospun matrix has an ultrastructure with a three-dimensional network that supports cell growth, proliferation, differentiation and development. The spatial distance between the fibers plays an important role in cells being able to obtain nutrients for growth as well as for allowing cell-cell interactions to occur. Thus, in various embodiments of the invention, the distance between the fibers may be about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 10 microns, 10 microns, 50 microns, about 100 microns, about 150 microns, about 200 microns, about 250 microns, about 300 microns, about 350 microns, about 400 microns, about 450 microns, or about 500 microns. In various embodiments the distance between the fibers may be less than 50 nanometers or greater than 500 microns and any length between the quoted ranges as well as integers.

Additionally, in various embodiments of the invention, the fibers can have a diameter of about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 50 microns, about 100 microns, about 150 microns, about 200 microns, about 250 microns, about 300 microns, about 350 microns, about 400 microns, about 450 microns, or about 500 microns, or the diameter may be less than 50 nanometers or greater than 500 microns and any diameter between the quoted ranges as well as integers.

The pore size in an electrospun matrix can also be controlled through manipulation of the composition of the material and the parameters of electrospinning. In some embodiments, the electrospun matrix has a pore size that is small enough to be impermeable to one or more types of cells. In one embodiment, the average pore diameter is about 500 nanometers or less. In another embodiment, the average pore diameter is about 1 micron or less. In another embodiment, the average pore diameter is about 2 microns or less. In another embodiment, the average pore diameter is about 5 microns or less. In another embodiment, the average pore diameter is about 8 microns or less. Some embodiments have pore sizes that do not impede cell infiltration. In another embodiment, the matrix has a pore size between about 0.1 and about 100 µm². In another embodiment, the matrix has a pore size between about 0.1 and about 50 µm². In another embodiment, the matrix has a pore size between about 1.0 µm and about 25 µm. In another embodiment, the matrix has a pore size between about 1.0 µm and about 5 µm. Infiltration can also be accomplished with implants with smaller pore sizes. The pore size of an electrospun matrix can be readily manipulated through control of process parameters, for example by controlling fiber deposition rate through electric field strength and mandrel motion, by varying solution concentration (and thus fiber size). Porosity can also be manipulated by mixing porogenic materials, such as salts or other extractable agents, the dissolution of which will leave holes of defined sizes in the matrix. The pore size can also be controlled by the amount of cross-linking present in the matrix.

The mechanical properties of the matrix will depend on the polymer molecular weight and polymer type/mixture. It will also depend on orientation of the fibers (preferential orientation can be obtained by changing speed of a rotating or translating surface during the fiber collection process), fiber diameter and entanglement. The cross-linking of the polymer will also effect its mechanical strength after the fabrication process.

The electrospun matrix can be cross linked to increase its stability and strength. The crosslinking can generally be conducted at room temperature and neutral pH conditions, however, the conditions may be varied to optimize the particular application and crosslinking chemistry utilized. For crosslinking using the EDC chemistry with NHS in MES/EtOH, pH of from 4.0 to 8.0 and temperatures from 0° C. to room temperature (25° C.) for two hours, can be used. It is known that higher temperatures are unpreferred for this chemistry due to decomposition of EDC. Similarly, basic pH (e.g., 8-14) is also unpreferred for this reason when using this chemistry. Other crosslinking chemistries can also be used for example, by soaking the electrospun matrix in 20% dextran solution (to reduce shrinking), followed by 1% glutaraldehyde solution. Yet other cross-linking chemistries involve using poly(ethylene glycol) (PEG) as a spacer in a crosslinking agent with an N-protected amino acid.

III. Synthetic Matrices

The invention also pertains to generating artificial tissue constructs by seeding cultured tissue cells onto or into available biocompatible matrices. Biocompatible refers to materials that do not have toxic or injurious effects on biological functions. Biodegradable refers to material that can be absorbed or degraded in a patient's body. Representative materials for forming the biodegradable material include natural or synthetic polymers, such as, collagen, poly(alpha esters) such as poly(lactate acid), poly(glycolic acid), polyorthoesters amd polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polyglactin, developed as absorbable synthetic suture material.

Polyglycolic acid and polyglactin fibers may be used as supplied by the manufacturer. Other biodegradable materials include, but are not limited to, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

In some embodiments, attachment of the cells to the biocompatible substrate is enhanced by coating the matrix with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. Mechanical and biochemical parameters ensure the matrix provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

Coating refers to coating or permeating a matrix with a material such as, liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix can be weaved, compression molded and glued together. Furthermore different polymeric materials shaped by different processes may be joined together to form a composite shape. The composite shape can be a laminar structure. For example, a polymeric matrix may be attached to one or more polymeric matrixes to form a multilayer polymeric matrix structure. The attachment may be performed by any suitable means such as gluing with a liquid polymer, stapling, suturing, or a combination of these methods. In addition, the polymeric matrix may be formed as a solid block and shaped by laser or other standard machining techniques to its desired final form. Laser shaping refers to the process of removing materials using a laser.

The polymers can be characterized for mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

Substrates can be treated with additives or drugs prior to implantation (before or after the polymeric substrate is seeded with cells), e.g., to promote the formation of new tissue after implantation. Thus, for example, growth factors, cytokines, extracellular matrix components, and other bioactive materials can be added to the substrate to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

The biocompatible substrate may be shaped using methods such as, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, the substrate is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the tissue. Next a solvent is used to dissolve away one of the components, resulting in pore formation. (See Mikos, U.S. Pat. No. 5,514,378, hereby incorporated by reference).

In nucleation, thin films in the shape of the tissue are exposed to radioactive fission products that create tracks of radiation damaged material. Next, the polycarbonate sheets are etched with acid or base, turning the tracks of radiation-damaged material into pores. Finally, a laser may be used to shape and burn individual holes through many materials to form a tissue structure with uniform pore sizes. The substrate can be fabricated to have a controlled pore structure that allows nutrients from the culture medium to reach the deposited cell population. In vitro cell attachment and cell viability can be assessed using scanning electron microscopy, histology and quantitative assessment with radioisotopes.

Thus, the substrate can be shaped into any number of desirable configurations to satisfy any number of overall system, geometry or space restrictions. The matrix can be shaped to different sizes to conform to the necessary structures of different sized patients.

A substrate can also be permeated with a material, for example liquified copolymers (poly-DL-lactide co-glycolide 50:50 80 mg/ml methylene chloride) to alter its mechanical properties. This can be performed by coating one layer, or multiple layers until the desired mechanical properties are achieved.

The substrate can also be treated or seeded with various factors and proteins to control the degradation/absorption of the matrix in the subject. For instance, if the cells seeded within the substrate are slow-growing, then it is beneficial to maintain the matrix integrity for a long enough period of time to allow the cells enough time to regenerate and grow. On the other hand, if the cells are able to quickly reproduce and grow, then a short lived substrate could be desirable. Varying the concentration of aprotinin additives, aminocaproic acid, tranxemic acid, or similar fibrinolytic inhibitors or the degree of chemical cross-linking in the matrix could be used to precisely control this variable. The substrate could also be seeded with varying growth factors such as angiogenesis factor to promote a growth of blood vessels upon implantation.

All types of matrices are preferably shaped into a tubular or cylindrical structures with length and diameter dimensions selected to correspond with digits or limbs of the subject. All types of matrices can be joined or bonded together or to a structural bone of the subject using standard techniques such as suturing, and gluing with biological glue. Suturing can involve known techniques using absorbable synthetic suture material such as the biocompatible polymer is polyglactin and polyglycolic acid, manufactured as Vicryl™ by Ethicon Co., Somerville, N.J. (See e.g., Craig P. H., Williams J. A., Davis K. W., et al.: A Biological Comparison of Polyglactin 910 and Polyglycolic Acid Synthetic Absorbable Sutures. Surg. 141; 1010, (1975)). Other methods of joining involve using biological glues. Biological glues can adhere to tissues, attach them to each other, or attach them to other structures on the body in a few minutes, without using staples or sutures. These glues are eliminated, in general after the cicatrization of the wound, by biodegradation, resorption or by simple detachment in the form of scabs.

Various technologies have been developed for the formulation of tissue adhesives. Some of them are of synthetic origin, such as the glues based on cyanoacrylates (2-butyl cyanoacrylate, 2-octyl cyanoacrylate), or on synthetic polymers, and others contain biological materials such as collagen or fibrin (See e.g., U.S. Pat. No. 5,844,016, U.S. Pat. No. 5,874,500; U.S. Pat. No. 5,744,545; U.S. Pat. No. 5,550,187 and U.S. Pat. No. 6,730,299).

IV. Intelligent Scaffolds

The invention pertains to using "intelligent" scaffolds that recruit cells, and encourage the formation of a vascular support and innervation via release of chemical factors. These intelligent scaffolds possess the necessary ultrastructural, biomechanical and biological characteristics are required for cell attachment, survival, neovascularization, innervation, and tissue maturation even in an environment with a limited blood supply. The intelligent scaffold can be created by adding any suitable therapeutic or biological agent such as genetic material, growth factors, cytokines, enzymes can be used to create an intelligent scaffold. The therapeutic or biological agent can recruit cells and factors that encourage growth and proliferation of cells seeded on the scaffold. These intelligent scaffolds can also be used to encourage nerve growth and innervation.

Examples of a therapeutic or biological agent include, but are not limited to proteins growth factors, antibodies, nucleic acids molecules, carbohydrates, and the like. Growth factors useful in the present invention include, but are not limited to, vascular endothelial growth factor (VEGF), nerve growth factors (NGF) including NGF 2.5 s, NGF 7.0 s and beta NGF and neurotrophis, transforming growth factor-alpha (TGF-α), transforming growth factor-beta (TGF-β), platelet-derived growth factors (PDGF), fibroblast growth factors (FGF), including FGF acidic isoforms 1 and 2, FGF basic form 2 and FGF 4, 8, 9 and 10, brain derived neurotrophic factor, cartilage derived factor, bone growth factors (BGF), basic fibroblast growth factor, insulin-like growth factor (IGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof.

Other molecules useful as therapeutic or biological agents include, but are not limited to, growth hormones, leptin, leukemia inhibitory factor (LIF), endostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon I alpha.

Embodiments involving amino acids, peptides, polypeptides, and proteins may include any type or combinations of such molecules of any size and complexity. Examples include, but are not limited to structural proteins, enzymes, and peptide hormones. These compounds can serve a variety of functions. In some embodiments, the matrix may contain peptides containing a sequence that suppresses enzyme activity through competition for the active site. In other applications antigenic agents that promote an immune response and invoke immunity can be incorporated into a construct. In substances such as nucleic acids, any nucleic acid can be present. Examples include, but are not limited to deoxyribonucleic acid (DNA), and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787, 567). DNA can be present in vectors of any kind, for example in a viral or plasmid vector. In some embodiments, nucleic acids used will serve to promote or to inhibit the expression of genes in cells inside and/or outside the electrospun matrix. The nucleic acids can be in any form that is effective to enhance its uptake into cells.

Factors involved in bone formation include hormones such as estrogen, calcitonin, and parathyroid hormone (PTH); growth factors such as bone morphologenic protein (BMP); and chemicals such as active vitamin D, calcium preparations, and vitamin K2. Estrogen, calcitonin, active vitamin D, and calcium preparations are used as medicine for controlling bone mass in osteoporosis or similar cases.

The intelligent scaffolds can be created by functionalizing the scaffold to incorporate a contrast enhancing agent (e.g., gadolinium) or a nanoparticles such as a quantum dot coupled to a biological or therapeutic agent. Quantum dots are a semiconductor nanocrystal with size-dependent optical and electronic properties. In particular, the band gap energy of a quantum dot varies with the diameter of the crystal. The average diameter of the QDs may be between about 1 to about 100 nm, between about 10-80 nm, and between about 25-40 nm. The coupled agent can be released by application of energy such as near infrared (NIR) irradiation from a laser source, which causes the bonds between the agent and the QD to break and thus releases the agent. This allows the release of the agent to be controlled by triggering its release upon application of energy. Quantum dots have been used as photostable biological fluorescent tags, semiconductors, and thermal therapy. The high transmission, scattering-limited attenuation, and minimal heating effects of quantum dots makes these suitable for the coupling of therapeutic/biological agents. In one embodiment, NIR CdSe quantum dots (Evident Technologies) can be used. These QDs have an optical absorption range of 700-1000 nm. NIR energy within this spectral region has been shown to penetrate tissue at depths up to 23 cm with no observable damage to the intervening tissue.

A matrix functionalized with a QD coupled to a therapeutic or biological agent can be used for controlled release of the therapeutic or biological agent at a target in the subject. The therapeutic or biological agent can be released by application of energy at a desired wavelength such as near infrared irradiation. Due to localized heating of the QD, ultrastructural changes cause the release of the coupled agent. The release kinetics can be varied according to the type of QD used and the wavelength of irradiation. The release kinetics can also be varied by altering the intensity and time of irradiation. For example, a QD (e.g., CdSe QD from Evident Technologies) coupled to encapsulated heparin can be incorporated into an electrospun matrix. Upon application of near infrared radiation at a wavelength of 700-1000 nm, the heparin is released in a controlled manner, as described in the examples below.

The studies in the examples section demonstrate the burst release of heparin over time when quantum dot conjugated heparin nanoparticles were irradiated by NIR irradiation. This system allows medical personnel to tune therapeutic/biological agent release rates post-operatively.

The emission spectra of quantum dots have linewidths as narrow as 25-30 nm depending on the size heterogeneity of the sample, and lineshapes that are symmetric, gaussian or nearly gaussian with an absence of a tailing region. The combination of tunability, narrow linewidths, and symmetric emission spectra without a tailing region provides for high resolution of multiply-sized quantum dots within a system and allows simultaneous examination of a variety of biological moieties tagged with QDs.

In addition, the range of excitation wavelengths of the quantum dots is broad and can be higher in energy than the emission wavelengths of all available quantum dots. Consequently, this allows the simultaneous excitation of all quantum dots in a system with a single light source. The ability to control the size of QDs enables one to construct QDs with fluorescent emissions at any wavelength in the UV-visible-IR region. Therefore, the colors (emissions) of QDs are tunable to any desired spectral wavelength. Furthermore, the emission spectra of monodisperse QDs have linewidths as narrow as 25-30 nm. The linewidths are dependent on the size heterogeneity of QDs in each preparation. In one embodiment, the QDs emit light in the ultraviolet wavelengths. In another embodiment, the QDs emit light in the visible wavelengths. In other embodiments, the QDs emit light in the near-infrared and the infrared wavelengths. Color of the light emitted by the QDs may be size-tunable and excitation energy tunable.

Many QDs are constructed of elements from groups II-VI, III-V and IV of the periodic table. They exhibit quantum confinement effects in their physical properties, and can be used in the composition of the invention. Exemplary materials suitable for use as quantum dots include, but are not limited to, ZnS, ZnSe, ZnTe, CdS, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof. The quantum dots may further include an overcoating layer of a semiconductor having a greater band gap.

In particular, the therapeutic or biological agent and the nanoparticles (e.g., quantum dot) can be entrapped or encapsulated to produce "nanocapsules." These nanocapsules containing the agent and the nanoparticle can be produce standard encapsulating techniques. Microencapsulation of agents generally involves three steps: (a) generating microcapsules enclosing the agents (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyomithine) to form a semipermeable membrane; and (c) liquefying the original core gel (e.g., by chelation using a solution of sodium citrate). The three steps are typically separated by washings in normal saline.

Alginates are linear polymers of mannuronic and guluronic acid residues. Monovalent cation alginate salts, e.g., Na-alginate, are generally soluble. Divalent cations such as $Ca^{2+}$, $Ba^{2+}$ or $Sr^{2+}$ tend to interact with guluronate, providing crosslinking and forming stable alginate gels. Alginate encapsulation techniques typically take advantage of the gelling of alginate in the presence of divalent cation solutions. Alginate encapsulation of agent-nanoparticles generally involves suspending the agent-nanoparticles to be encapsulated in a solution of a monovalent cation alginate salt, generating droplets of this solution, and contacting the droplets with a solution of divalent cations. The divalent cations interact with the alginate at the phase transition between the droplet and the divalent cation solution, resulting in the formation of a stable alginate gel matrix being formed. A variation of this technique is reported in U.S. Pat. No. 5,738,876, where the cell is suffused with a solution of multivalent ions (e.g., divalent cations) and then suspended in a solution of gelling polymer (e.g., alginate), to provide a coating of the polymer.

Another method of microencapsulating agent-nanoparticles is the alginate-polyamino acid technique. Cells are suspended in sodium alginate in saline, and droplets containing islets are produced. Droplets of cell-containing alginate flow into calcium chloride in saline. The negatively charged alginate droplets bind calcium and form a calcium alginate gel. The microcapsules are washed in saline and incubated with poly-L-lysine (PLL) or poly-L-ornithine (or combinations thereof); the positively charged poly-l-lysine and/or poly-L-ornithine displaces calcium ions and binds (ionic) negatively charged alginate, producing an outer poly-electrolyte membrane. A final coating of sodium alginate may be added by washing the microcapsules with a solution of sodium alginate, which ionically bonds to the poly-L-lysine and/or poly-L-ornithine layer. See U.S. Pat. No. 4,391,909 to Lim et al (all U.S. patents referenced herein are intended to be incorporated herein in their entirety). This technique produces what has been termed a "single-wall" microcapsule. Preferred microcapsules are essentially round, small, and uniform in size. (Wolters et al., *J. Appli Biomater.* 3:281 (1992)).

The alginate-polylysine microcapsules can also then be incubated in sodium citrate to solubilize any calcium alginate that has not reacted with poly-l-lysine, i.e., to solubilize the internal core of sodium alginate containing the islet cells, thus producing a microcapsule with a liquefied cell-containing core portion. See Lim and Sun, Science 210:908 (1980). Such microcapsules are referred to herein as having "chelated", "hollow" or "liquid" cores. A "double-wall" microcapsule is produced by following the same procedure as for single-wall microcapsules, but prior to any incubation with sodium citrate, the microcapsules are again incubated with poly-l-lysine and sodium alginate.

Many alternative techniques used for encapsulating agents are known in the art and can be used with this invention. U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-l-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

In one embodiment, heparin is coupled to the nanoparticle and the controlled release kinetics of heparin can be monitored. One skilled in the art will appreciate that the control release kinetics depend on the capsulation parameters including nanocapsule size, heparin and quantum dot loading, and polymer composition. The mean diameter of the nanocapsules depends on the mixing velocity of the preparation process and viscosity of the preparation media. Nanocapsule size can be reduced by exposing the preparation to sonication over a range of about 30 second to about 120 seconds, increasing the sonication intensity from about 5 watts to about 20 watts, or by varying the ratios of organic polymer phase to aqueous heparin phase. Nanocapsule sizes can be characterized by scanning electron microscopy (SEM), coulter counter, and light scattering.

In one embodiment, the heparin can be conjugated to quantum dots by using an EDC/NHS chemical method. Various concentrations of heparin (ranging form 10-30 weight % polymer) and quantum dots can be used to determine optimal loading efficiency.

For polymer encapsulation, FDA approved biodegradable polymers (PLA, PLGA, PCL) can be used for the control of encapsulation and degradation of the nanocapsules in vivo.

The examples show that a burst of heparin release occurs using a broadband infrared (IR) source. Using measured quantities of QD-Heparin nanocapsules (NC) suspended in a physiological buffer, the influence of varying wavelengths, intensities, and irradiation times on the release kinetics can be determined. In one embodiment, the wavelength of irradiation used on the QD-Heparin can be in the near-infrared wavelength range, such as 700 nm, 800 nm, and 900 nm, using a filtered xenon source. The intensity of irradiation energy can be adjusted in incremental steps from 0 (control), 1 $mW/cm^2$, 10 $mW/cm^2$, 100 $mW/cm^2$, 1 $W/cm^2$, and 10 $W/cm^2$. The irradiation time can also be varied to determine the optimal irradiation time at each effective power intensity. The irradiation time can vary from 0 (control), 10, 60, 300, and 600 seconds of exposure.

The encapsulated QD-heparin will be released upon near infra-red (NIR) irradiation due to localized heating of the quantum dots which induces ultrastructural changes in the nanocapsules. The release kinetics will be varied at the target site by modulating the intensity and time of NIR irradiation to produce a controlled release of heparin. The quantitative measurement of heparin released from the nanocapsules can be measured over time (2, 4, 6, 12, and 24 hours and daily thereafter up to 30 days) and measured for its anti-factor Xa activity with a synthetic chromogenic substrate using a kit Rotachrom (Diagnostica Stago Inc).

The scaffold may also be functionalized with an image enhancing agent to monitor growth and assimilation of the construct in vivo. In another aspect, the invention pertains to monitoring tissue remodeling a tissue engineered construct. Remodeling that takes place too slowly can result in pathologic response of surrounding tissues and compliance mismatch of the vessel. Rapid remodeling can result in premature failure of the engineered construct. Magnetic Resonance Imaging (MRI) is a powerful, non-invasive technique that can be used long term for monitoring the remodeling process. Nanoparticles (e.g., QD, image enhancing agents) can be easily bound to matrices, and also embedded within nanofibers of electrospun matrices. The nanoparticles provide high MRI contrast, and due to their small size, will not interfere with normal biological processes. Organolanthanide complexes containing paramagnetic metals such as gadolinium (Gd) have been known to cause distortion in an electromagnetic field. When the protons in water interact with this distorted field, their magnetic properties significantly change such that they can be detected by MRI. The Examples demonstrate the enhanced imaging observed using MRI contrast with Gd functionalized nanoparticles bound to the surface and/or incorporated into the vascular matrices or nanocapsules. Other examples of contrast enhancing agents include, but are not limited to, rare earth metals such as, cerium, samarium, terbium, erbium, lutetium, scandium, barium, bismuth, cerium, dysprosium, europium, hafnium, indium, lanthanum, neodymium, niobium, praseodymium, strontium, tantalum, ytterbium, yttrium, and zirconium.

In one embodiment, the agents are joined to the matrix by peptide bonds. For example, nanoparticles can be incorporated as part of the matrix using EDC (1-ethyl-3(3-dimethly aminopropyl)carbodiimide) and sulfo-NHS (N-hydrocyl-sulfo-succinimide) to form peptide bonds. Various other know techniques can be used as described, for example, in Heumanson, Bioconjugate Techniques, Academic Press San Diego, Calif., 1996, herein incorporated by reference. For external functionalization, a peptide bond can be created between the matrix and carboxylated gadolinium nanoparticles using the EDC/sulpho-NHS method to form peptide bonds between the carboxylates and amino groups. The quantum dot coupled to a therapeutic/biological agent, a contrast enhancing agent, e.g., gadolinium, or both, can also be added internally to an electrospun matrix by incorporating each component into the solution with at least one natural compound and at least one synthetic compound. For example, solutions containing collagen I, elastin and PLGA, successfully incorporated the contrast enhancing agent gadolinium upon electrospinning as described in the Examples. The incorporation of the gadolinium into the matrix can be observed in vitro and in vivo using detection methods such as magnetic resonance imaging (MRI). Thus, a matrix functionalized with a contrasting agent allows the degradation of the matrix to be monitored.

Any type of functionalization method can be used. Examples of some possible functionalization chemistries include, but are not limited to, esterification (e.g., with acyl halides, acid anhydrides, carboxylic acids, or esters via interchange reactions), ether formation (for example, via the Williamson ether synthesis), urethane formation via reactions with isocyanates, sulfonation with, for example, chlorosulfonic acid, and reaction of b-sulfato-ethylsulfonyl aniline to afford an amine derivative that can be converted to a diazo for reaction with a wide variety of compounds. Such chemistries can be used to attach a wide variety of substances to the electrospun matrix, including but not limited to crown ethers (Kimura et al., (1983) *J. Polym. Sci.* 21, 2777), enzymes (Chase et al. (1998) *Biotechnol. Appl. Biochem.*, 27, 205), and nucleotides (Overberger et al. (1989) *J. Polym. Sci.* 27, 3589).

V. Composite Scaffolding

Numerous materials can be used as scaffolds for bone tissue reconstruction as described above. These include metals, ceramics and polymers from biologic and synthetic origins. Synthetic materials, such as hydroxyapatite (HA), tricalcium phosphate (TCP), calcium sulfate, poly(lactide-co-glycolide) (PLGA), polyglycolide (PGA) and polylactide (PLA) can be used either alone or in combination with naturally derived materials including collagen, chitosan, starch and silk fibroin. These materials are designed to serve as a bone substitute or as an enhancement for the bone healing process. Among the several commercially available bone graft materials, Collagraft (collagen-hydroxyapatite composite scaffold) is currently the most commonly used material clinically.

In some embodiments, a cell-based approach can be used in bone tissue regeneration. While many biomaterials serve as a scaffold that augments the body's ability to heal itself, a tissue engineering approach uses cells added to a scaffold to achieve formation of bone tissue. Existing biomaterials, such as Collagraft, may not be ideal for use with cells due to their physical and structural configuration, which includes low cell adhesion, poor cell infiltration and brittleness. PLGA has been used as a scaffold for bone tissue engineering due to its favorable physical properties. However, the surface chemistry of PGLA does not fully promote cell adhesion and proliferation due to its hydrophobic nature.

In one aspect, the invention discloses composite bone scaffolds comprising a biodegradable synthetic polymer and a naturally derived collagen matrix. Examples of synthetic polymers include, but are not limited to, poly(lactide-co-glycolide) (PLGA), poly(lactide) (PLA), poly(glycolic acid) (PGA), poly(caprolactone), polycarbonates, polyamides, polyanhydrides, polyamino acids, polyortho esters, polyacetals, polycyanoacrylates, degradable polyurethanes, hydroxyapatite (HA), tricalcium phosphate (TCP), and calcium sulfate. Examples of a naturally derived collagen matrix suitable for the present invention include, but are not limited to, submucosa, such as bladder, stomach, esophagus, stomach, small intestine, large intestine (colon) submucosa. The submucosa is a layer of interstitial protein that supports blood vessels, which supply the mucosa with nutrients and the lymph nodes which aid in the removal of waste products. The submucosa serves an important function, and is produced as the interface between the mucosa and the detrusor. Many organs are made up of multiple layers of different tissues. Depending on the functional role of the organ, different tissues confer different properties to the organ. For example, the bladder has three main layers of tissue: the mucosa, submucosa and detrusor. The submucosa can be harvested from a mammal (i.e., human, cow, pig, etc.) as described below.

The biocompatible composite scaffolding system preferably has a substantially uniform porous structures having an average pore diameter ranging from about 50 to about 250 µm, preferably from about 90 to about 150 µm, and most preferably from about 110 to about 130 µm. The porosity of the biocompatible composite scaffolding is greater than about 50%, preferably greater than about 80%, more preferably greater than about 90%, and most preferably greater than about 95%.

In another aspect, the invention provides a method of fabricating a biocompatible composite scaffolding system capable of providing structural support for regenerated bone tissue comprising selecting a pore size, obtaining porogens of said selected size, adding the porogens to a solution containing a synthetic polymer and submucosa and mixing to distribute said porogens and form a composite scaffold, drying said composite scaffold to remove residual solvent, and removing said porogens from said composite scaffold. The method can further include sieving porogens through a sieve to obtain said selected size porogens. The step of removing said porogens from said composite scaffold can comprise immersion in water. As used here, the term "porogen" refers to any soluble particulate. Some exemplary porogen materials suitable for use in the present invention are selected from the group consisting of salts including, but not limited to sodium chloride, potassium chloride, sodium fluoride, potassium fluoride, sodium iodide, sodium nitrate, sodium sulfate, sodium iodate, and mixtures thereof, other water soluble chemicals such as sodium hydroxide, sugars including, but not limited to saccharin, glucose, fructose, other water soluble sugars, and mixtures thereof, waxes paraffin, beeswax, other waxes, and mixtures thereof, gelatins, naphthalene, natural or synthetic water soluble polymers, natural or synthetic non-water soluble polymers, degradable polymers, non-degradable polymers, partially degradable polymers, and mixtures thereof. The porogen materials can be formed into any shape as desired and/or necessary. However, in the preferred embodiment, the predetermined shape is selected from the group consisting of cubic or other geometrically shaped crystals, spheres, fibers, discs, regular geometric shapes, irregular geometric shapes, and mixtures thereof. A preferred porogen is sodium chloride. The synthetic polymer can be selected from the group comprising poly(lactide-co-glycolide) (PLGA), poly(lactide) (PLA), poly(glycolic acid) (PGA), poly(caprolactone), polycarbonates, polyamides, polyanhydrides, polyamino acids, polyortho esters, polyacetals, polycyanoacrylates, degradable polyurethanes, hydroxyapatite (HA), tricalcium phosphate (TCP), and calcium sulfate. In a preferred embodiment, the synthetic polymer is poly(D,L-lactide-co-glycolide) (PLGA) and the submucosa is bladder submucosa (BSM). The preferred weight ratio of PLGA and BSM to NaCl is about 1:10, but can range from about 1:5 to about 1:30.

The composite scaffolds are configured to accommodate cells and designed to provide adequate structural support. The biological activity, physical and structural properties of the scaffolds for their use in bone tissue regeneration using two different cell types were confirmed as shown in Example 28.

Primary mature osteoblasts and stem cells form bone tissues when implanted in vivo or differentiated into bone cells. These cell types were used to determine their ability to survive, adhere and proliferate on the composite scaffolds. Cell accommodation, adhesion and proliferation were approximately 80% higher in the BSM-PLGA composite scaffolds, as compared to the control scaffolds using these two cell types. Fabrication of the scaffolds with an appropriate pore size, porosity and surface hydrophilicity resulted in abundant cell accommodation with increased cell proliferation. The incorporation of BSM significantly improved the biological activities of the scaffold, while maintaining physical and structural stability.

Creation of bone tissue using cells requires a scaffold that serves as a cell carrier which would provide structural support until bone tissue forms in vivo. The scaffold for bone tissue engineering should be biocompatible and possess mechanical stability, a controlled degradation rate, hydrophilic surface chemistry and an appropriate porosity for cell accommodation. In one embodiment of this invention, a composite scaffold for bone regeneration is disclosed that meets these criteria by hybridizing BSM as a natural bioactive material with synthetic PLGA polymers. Example 28 demonstrates that the biodegradable synthetic polymer and naturally derived collagen matrix composite scaffolds are non-toxic, easily fabricated, and provide structural support with abundant pores with good interconnectivity.

A scaffold material for bone regeneration should be biocompatible and safe for implantation. Cellular interactions of the BSM-PLGA composite scaffold were tested by using the two widely accepted complementary assays; cell viability and mitochondrial metabolic activity. The cell viability assay using Neutral Red, which is based on dye incorporation into lysosomes, and the MTT assay, which is based on the intact activity of a mitochondrial enzyme, demonstrated that the BSM-PLGA composite scaffolds are safe.

VI. Culturing Cells

To engineer a limb tissue composed of a patient's own cells, a reliable cell expansion system for each cell type was established. Stem and progenitor cells in particular, muscle progenitor cells (MPC) are an ideal cell source for tissue engineering. These cells have the capacity of self renewal and are multipotent i.e. they are able to differentiate into a wide variety of cell types and tissues. Adult stem and progenitor cells can be isolated from various sources. In addition to "tissue specific" stem cells found to reside within a number of adult tissues, the bone marrow stroma provides a "universal" source of stem cells that participate in regenerative processes of many tissues. Stem and progenitor cells from various stages of development, have been used including embryonic, fetal and adult, from multiple tissue sources. A system has been established to differentiate adult stem cells into bone, muscle, fat, endothelial and nerve cells. These cells were further transplanted and formed functional tissues in vivo.

Bone marrow stem cells can also be used for the engineering of bone tissues of the digit. Bone marrow cells can be easily obtained through a simple needle aspiration and density gradient centrifugation. The bone marrow cells will be expanded in culture, characterized and induced to become bone cells in the presence of osteogenic supplements. The phenotypic and functional characteristics of the bone cells can be determined by evaluation of alkaline phosphatase production and activity, calcium deposition and mineralization.

Muscle cells e.g. myoblasts, can be obtained from a skeletal muscle tissue biopsy. MPC migrated from the single fibers will be grown and expanded. Phenotypical and functional assessment of the myoblasts includes testing their ability to form myotubes, as well as Western blot, RT-PCR and immunohistochemical analyses. Myoblasts can be seeded on muscle scaffolds for tissue formation in vitro. The engineered bone and muscle composite tissues can be assessed for their structural, physical and physiological characteristics.

There are five main types of bone cells in bone tissue. Osteogenic cells respond to traumas, such as fractures, by giving rise to bone-forming cells and bone-destroying cells. Osteoblasts (bone-forming cells) synthesize and secrete unmineralized ground substance and are found in areas of high metabolism within the bone. Osteocytes are mature bone cells made from osteoblasts that have made bone tissue around themselves. These cells maintain healthy bone tissue by secreting enzymes and controlling the bone mineral content; they also control the calcium release from the bone tissue to the blood. Osteoclasts are large cells that break down bone tissue. They are very important to bone growth, healing, and remodeling. The last type of cells are bone-lining cells. These are made from osteoblasts along the surface of most bones in an adult. Bone-lining cells are thought to regulate the movement of calcium and phosphate into and out of the bone. For cartilage cells, chondrocytes and chondroblasts can be used.

The artificial tissue can be created by using allogenic cell populations derived from the subject's own tissue. The artificial tissue can also be xenogenic, where cell populations are derived from a mammalian species that are different from the subject. For example, muscle, cartilage-forming or bone-forming tissue cells can be derived from mammals such as monkeys, dogs, cats, mice, rats, cows, horses, pigs, goats and sheep.

The isolated cells are preferably cells obtained by a swab or biopsy, from the subject's own tissue. A biopsy can be obtained by using a biopsy needle under a local anesthetic, which makes the procedure quick and simple. The small biopsy core of the isolated tissue can then be expanded and cultured to obtain the tissue cells. Cells from relatives or other donors of the same species can also be used with appropriate immunosuppression.

Methods for the isolation and culture of cells are discussed by Freshney, Culture of Animal Cells. A Manual of Basic Technique, 2d Ed., A. R. Liss, Inc., New York, 1987, Ch. 9, pp. 107-126. Cells may be isolated using techniques known to those skilled in the art. For example, the tissue can be cut into pieces, disaggregated mechanically and/or treated with digestive enzymes and/or chelating agents that weaken the connections between neighboring cells making it possible to disperse the tissue into a suspension of individual cells without appreciable cell breakage. If necessary, enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the tissue, the use of grinders, blenders, sieves, homogenizers, pressure cells, or insonators to name but a few.

Cell types include, but are not limited to, progenitor cells isolated from the peripheral blood or bone marrow cells that can be induced to differentiate into different cells such as muscle cells, bone cells or cartilage cells, stem cells, committed stem cells, and/or differentiated cells may be used. Also, depending on the type of tissue or organ being made, specific types of committed stem cells can be used. For instance, myoblast cells can be used to build various muscle structures. Other cells include, but are not limited to, endothelial cells, muscle cells, smooth muscle cells, fibroblasts, osteoblasts, myoblasts, neuroblasts, fibroblasts, glioblasts; germ cells, hepatocytes, chondrocytes, keratinocytes, cardiac muscle cells, connective tissue cells, epithelial cells, endothelial cells, hormone-secreting cells, cells of the immune system, neurons, and the like.

Examples also include cells that have been genetically engineered, transformed cells, and immortalized cells. One example of genetically engineered cells useful in the present invention is a genetically engineered cell that makes and secretes one or more desired molecules. When matrices comprising genetically engineered cells are implanted in an organism, the molecules produced can produce a local effect or a systemic effect, and can include the molecules identified above as possible substances.

Cells may produce substances that inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace the following tissue, neurons, skin, synovial fluid, tendons, cartilage, ligaments, bone, muscle, organs, dura, blood vessels, bone marrow, and extracellular matrix.

The shape of the extracellular matrix may help send signals to the cells to grow and reproduce in a specific type of desired way. Other factors and differentiation inducers may be added to the matrix to promote specific types of cell growth.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting (see e.g. Freshney, (1987) Culture of Animal Cells. A Manual of Basic Techniques, 2d Ed., A. R. Liss, Inc., New York, Ch. 11 and 12, pp. 137-168). For example, salivary cells may be enriched by fluorescence-activated cell sorting. Magnetic sorting may also be used. The cells may also be isolated using magnetic selection techniques.

Cell fractionation may also be desirable, for example, when the donor has diseases such as cancer or tumor. A cell population may be sorted to separate the cancer or tumor cells from normal noncancerous cells. The normal noncancerous cells, isolated from one or more sorting techniques, may then be used for tissue reconstruction.

Isolated cells can be cultured in vitro to increase the number of cells available for seeding into the biocompatible substrate. To prevent an immunological response after implantation of the artificial gift or limb composite tissue construct, the subject may be treated with immunosuppressive agents such as, cyclosporin or FK506.

Isolated cells may be transfected with a nucleic acid sequence. Useful nucleic acid sequences may be, for example, genetic sequences which reduce or eliminate an immune response in the host. For example, the expression of cell surface antigens such as class I and class H histocompatibility antigens may be suppressed. In addition, transfection could also be used for gene delivery. Cells may be transfected with specific genes prior to seeding onto the biocompatible substitute. Thus, the cultured cells can be engineered to express gene products that would produce a desired protein that helps ameliorate a particular disorder.

The tissue cells grown on the matrix substrate may be genetically engineered to produce gene products beneficial to implantation, e.g., anti-inflammatory factors, e.g., anti-GM-CSF, anti-TNF, anti-IL-1, and anti-IL-2. Alternatively, the tissue cells may be genetically engineered to "knock out" expression of native gene products that promote inflammation, e.g., GM-CSF, TNF, IL-1, IL-2, or "knock out" expression of MHC in order to lower the risk of rejection.

Methods for genetically engineering cells for example with retroviral vectors, adenoviral vectors, adeno-associated viral vectors, polyethylene glycol, or other methods known to those skilled in the art can be used. These include using expression vectors which transport and express nucleic acid molecules in the cells. (See Geoddel; *Gene Expression Technology: Methods in Enzymology* 185, Academic Press, San Diego, Calif. (1990).

Vector DNA is introduced into prokaryotic or eukaryotic cells via conventional transformation or transfection techniques. Suitable methods for transforming or transfecting host cells can be found in Sambrook et al. *Molecular Cloning: A Laboratory Manual,* 2nd Edition, Cold Spring Harbor Laboratory press (1989), and other laboratory textbooks.

Once seeded onto the matrix, the cells will proliferate and develop on the matrix to form a tissue layer. Importantly, because the matrix has an infra-structure that permits culture medium to reach the tissue layer, the cell population continues to grow, divide, and remain functionally active to develop into a tissue that has a morphology which resembles the analogous structure in vivo.

It is important to recreate, in culture, the cellular microenvironment found in vivo for the particular tissue being engineered. By using a matrix that retains an infra-structure that is similar or the same as an in vivo tissue structure, the optimum environment for cell-cell interactions, development and differentiation of cell populations, is created.

Growth factors and regulatory factors can be added to the media to enhance, alter or modulate proliferation and cell maturation and differentiation in the cultures. The growth and activity of cells in culture can be affected by a variety of growth factors such as growth hormone, somatomedins, colony stimulating factors, erythropoietin, epidermal growth factor, hepatic erythropoietic factor (hepatopoietin), and like. Other factors which regulate proliferation and/or differentiation include prostaglandins, interleukins, and naturally-occurring chalones.

The artificial tissue constructs of the invention can be used in a variety of applications. For example, the artificial tissue constructs can be implanted into a subject to replace or augment existing tissue. The subject can be monitored after implantation of the artificial tissue or organ, for amelioration of the disorder.

Other embodiments and used of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

EXAMPLES

Example 1

Methods and Materials (i) Scaffold Preparation

Electrospun nanofiber scaffolds have been developed using a solution of collagen type I, elastin, and poly(D,L-lactide-co-glycolide) (PLGA, mol. ratio 50:50, Mw 110,000) (Boeringer-Ingelheim, Germany). Collagen type I from calf skin (Elastin Products Company, Owensville, Mo.), elastin from ligamentum nuchae (bovine neck ligament), (Elastin Products Company, Owensville, Mo.), and PLGA are mixed at a relative concentration by weight of 45% collagen, 40% PLGA, and 15% elastin. The solutes are dissolved in 1,1,1,3,3,3-hexafluoro-2-propanol (99+ %) (Sigma Chemical Company, St. Louis, Mo.) at a total solution concentration of 15 w/v % (150 mg/mL). High molecular weight PLGA, previously used for electrospinning tissue scaffolds is added to the solution to increase mechanical strength of the scaffold and increase viscosity and spinning characteristics of the solution.

Physically, the electrospinning method requires a high voltage power supply, a syringe pump, a polymer solution or melt to be spun, and a grounded collection surface. During electrospinning, the grounded mandrel rotates while the stage translates to ensure even deposition of fibers onto the mandrel surface. Solutions were electrospun using a high voltage power supply (Spellman High Voltage, Hauppauge, N.Y.) at 25 kV potential between the solution tip and the grounded surface. The solution was delivered with a 5 mL syringe through an 18 gauge blunt tip needle at a flow rate of 3.0 mL/hr using a syringe pump. Fibers collect onto a grounded mandrel at a distance of 15 cm from the tip. The mandrel is a 303 stainless steel rod which is rotated at ~500 rpm. The mandrel size is initially 4.75 mm to allow for contraction of the graft due to crosslinking. Uniform scaffolds of 120 mm length were created using 2.4 mL of solution. This apparatus is shown schematically in FIG. 1.

Scaffolds were further crosslinked for increased stability and strength, using two crosslinking methods. The scaffolds were soaked for two minutes in 20% dextran solution in phosphate buffered saline prior to crosslinking to reduce hydration-induced swelling and contraction of the scaffold. The scaffolds were crosslinked by immersion in 1) 1% glutaraldehyde solution and 2) EDC/NHS in MES/EtOH solution for 2 hours at room temperature. These data show that it is possible to fabricate vascular scaffolds from biological polymers with mechanics and structure similar to decellularized scaffolds and native arteries.

FIG. 1. shows the electrospinning apparatus in which fibers deposit onto a grounded collection surface as solvent evaporates due to increasing surface area/volume ratio of solution. The electrostatic field causes splaying of solution, and solutions of sufficient viscosity and surface tension form fibrous mats which adhere to grounded surfaces.

(ii) Cell Seeding

A confluent monolayer of endothelial cells is the most important barrier against thrombus formation, and endothelial cell mediated NO production is important to maintain vascular tone. Cells were seeded with a mouse endothelial cell line MS 1 cells. The cells routinely cultured in tissue culture polystyrene flasks at 37° C. under 5% CO2 atmosphere were harvested after the treatment with 0.1% trypsin-EDTA. The scaffolds were mounted in tissue culture dishes. After equilibration with PBS, the cells ($1\times10^5$/mL) were seeded to the scaffolds. The culture medium used was DMEM medium containing 10% FBS, and antibiotics. After 2 days culture, the cell attachment was assessed using scanning electron microscopy.

(iii) Microscopy

The relative quantity and distribution of collagen and elastin in a vascular scaffold is important to the mechanical properties and function of the seeded graft. To determine the distribution of components of the scaffolds, histo- and immunohistochemical analyses were performed to identify collagen and elastin distribution.

(iv) Biocompatibility Testing (Cell Viability and Proliferation)

Long-term viability of cells is necessary for the seeded scaffold to remodel itself into a viable, patent vessel. Standard methods were employed to assess viability and proliferation. To test for cell viability, constructs were placed in 24-well plates with approximately 100 mg of material per well. Four different types of material were tested for biocompatibility and cell survival, with one negative control well with no material: (1) GA-NFS (1% glutaraldehyde crosslinked electrospun scaffold); (2) EDC-NFS (EDC-crosslinked electrospun scaffold); (3) nBV (natural blood vessel, decellularized); (4) Latex (latex rubber, positive control).

Endothelial cells were seeded in the wells on a scaffold for testing via the direct contact method. For cell viability, cell layers were rinsed with PBS. 0.005% w/v neutral red was added in culture medium. The neutral red solution was removed after 4 hours incubation at 37° C. with 1% acetic acid and 50% ethanol solution by volume was added for dye extraction, and dye extraction was shaken for 5 minutes. Absorbance was then measured at 540 nm using a spectrophotometer. The intensity of red color obtained was directly proportional to the viability of the cells and inversely proportional to the toxicity of the material.

Cell proliferation was tested using the mitochondrial metabolic activity assay. Cell layers were first rinsed with PBS. MTT solution was added at 1 mg/mL in PBS containing 1 mg/mL glucose. MTT solution was removed after 4 hours incubation at 37° C. Dimethyl sulfoxide (DMSO) was used to dissolve insoluble formazan crystals, and the absorbance at 540 nm was measured using a spectrophotometer. The intensity of blue color was directly proportional to the metabolic activity of the cell populations and inversely proportional to the toxicity of the material or extract.

(v) Mechanical Testing

Compliance mismatch is one of the most common causes of vascular graft failure, resulting in intimal hyperplasia and occlusion. If the scaffold is too compliant, it may form an aneurysm.

Scaffolds were immersed in a water bath and cannulated at either end. One cannula was connected to a column of water and the other to a drainage tube. The column of water was high enough to create a pressure within the vessel-shaped scaffold of 120 mmHg. Water was drained through the scaffold in order to lower the pressure in increments of 10 mmHg. At each increment, the diameter of the scaffold was recorded using a digital camera. This process was repeated until the pressure was 0 mmHg.

(vi) Axial and Circumferential Segment Testing

Vessels must resist higher stress in the circumferential direction than in the axial direction. Native vessels adapt their mechanics to this loading environment. It is important that the electrospun scaffolds exhibit a mechanical strength at least that of native vessels. We performed mechanical loading tests on the electrospun vessels in the axial and circumferential directions using a uniaxial load test machine (Instron Corporation, Issaquah, Wash.). A short segment from a tubular scaffold was clamped at its cut ends for the axial test. The crosshead speed was set at 0.5 mm/sec and the test was stopped when the strain decreased by 10% after the onset of failure. For testing in the circumferential direction, a ring of material was cut from the scaffold, opened into a strip and then clamped at either end of the strip. This test was also performed at a rate of 0.5 mm/sec.

(vii) Burst Pressure Testing

The burst pressure for vascular scaffolds was found by monitoring increasing pressures within the vessel until failure occurred. A pressure catheter was inserted through a cannulating fixture at one end of the vessel. A 60 cc pressure syringe was inserted through a custom cannula at the other end of the vessel. The pressure was increased until failure or leakage occurred and the pressure change was recorded.

(viii) Functionalization of Matrices

Figure 2:
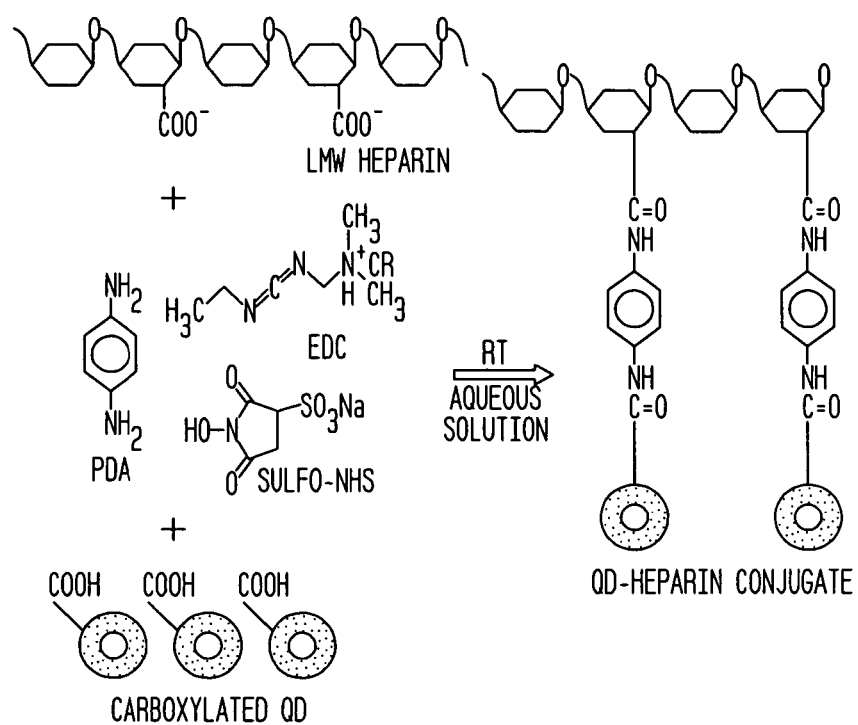
FIG. 2 is a schematic of the conjugation of heparin on quantum dots.

To functionalize a matrix, EDC (10 mg) and sulfo-NHS (2 mg) were added to 5 mL (0.05 mg/mL) of carboxylated quantum dots in aqueous solution under gentle stirring for 1 hr at room temperature. EDC activated heparin (30 mg/20 µl) was prepared according to the same EDC and NHS method. In order to conjugate quantum dots and heparin, 5 mg PDA was added to the activated quantum dots and heparin solutions under stirring for 2 hr at room temperature. The quantum dot-heparin (QD-heparin) conjugation can be quenched by adding an equal volume of 1 M Tris buffer solution (pH 7.4) and stored in 4° C. (FIG. 2).

(ix) Encapsulation

Microencapsulation of QD-heparin was performed by double emersion. Briefly, 4 mL of internal aqueous phase containing 30 mg QD-heparin and 10 mg bovine serum albumin (BSA) as stabilizer was emulsified in 8 ml solution of 100 mg PLGA and 100 mg PCL in dichloromethane. The solution was emulsified by vortexing for 5 minutes at room temperature. This W/O dispersion was diluted to 200 ml of 1% (w/v) aqueous PVA solution under stirring for 4 hr at room temperature. The microcapsules were washed several times with deionized water and then lyophilized overnight.

(x) Heparin Release using IR Irradiation of the Quantum Dot

In order to evaluate the burst release of heparin, 0.55 mg of PLGA microcapsules containing QD-heparin were suspended in 2 ml of PBS (phosphate buffered saline). The solution was irradiated for 0, 10 and 30 min using an AM1.5 solar simulator at 75 mW/cm2. On days 1, 3 and 5, the samples were then cooled to 4° C., centrifuged at 4500 rpm for 20 min and filtered (0.45 µm pore size) to remove any microcapsules for the optical measurements. Luminescence measurements were performed using an argon ion laser (514.5 nm at 400 mW/cm2) as the excitation source and spectra were collected using a CCD spectrophotometer with an integration time of 40 sec.

(xi) Mouse Model

Mice (C57BL6) will be obtained from Jackson laboratories, Bar Harbor Me. All experimentation in mice will be performed aseptically under general anesthesia (ketamine; 45-75 mg/kg and Xylazine; 10-20 mg/kg, IP). The incision sites are scrubbed with betadine and wiped with alcohol. Analgesia (Buprenorphine 0.05-0.1 mg/kg, SC) is given postoperatively after implantation. Prophylactic antibiotic agents (cefazoline 25 mg/kg, sc) are given to the animals at the time of implantation. The prepared blood vessels (2×0.5 cm) will be implanted in the dorsal subcutaneous space of mice through a minimal longitudinal midline incision with 2 implants per animal. The wound will be closed with interrupted absorbable sutures and the animals will be sacrificed 1, 2, 4, 8, 12, 18 and 24 weeks after implantation for analyses.

For the collection of blood samples, mice will be anesthetized and blood will be retrieved into heparin containing tubes using cardiac puncture and the mice will be sacrificed thereafter.

(xii) Sheep Model

A total of 120 sheep will be used. The experimental study will consist of 6 different groups of the blood vessels. Each animal will serve as its own control. Animals will be sacrificed at 1, 3, 6, 12, and 18 months after implantation. Animals will be monitored at 0, 1, 2, 3, and 4 weeks and monthly for grafts implanted greater than one month.

Sheep will be sedated with Ketamine (5 mg/kg, IM), intubated and anesthetized with Isofluorane (1-3%), and placed on a ventilator administering Isoflurane for maintenance. Following Duplex ultrasound imaging of native femoral arteries the groins will be prepped in a sterile fashion and antibiotics administered (cefazolin 25 mg/kg, i.v.). A longitudinal incision will be made overlying the superficial femoral artery, which will then be exposed over a length of 6 to 8 cm. Animals will receive aspirin for 48 hours prior to surgery (80 mg, p.o.) and heparin will be administered immediately prior to implantation (100 U/Kg, i.v.). The femoral artery will then be clamped and divided proximally and an end-to-side anastomosis created between native and engineered artery with running 7-0 Prolene sutures. The distal anastomosis will then be created in a similar fashion and blood flow restored through the implant. Duplex ultrasound will then be repeated using a sterile intraoperative probe cover to establish artery dimensions and blood flow immediately after implantation. Wounds will then be closed with absorbable sutures and the animals recovered from anesthesia using Atropine (0.02 mg/kg i.v.) prior return to standard housing. Post-operative antibiotics will be administered (Cephazoline 25 mg/kg/day) for 3 days following the procedure. Analgesia will be administered (ketoprofen 2 mg/kg) every 6-12 hours for 3 days. Aspirin will also be administered (80 mg daily) for 7 days orally for anticoagulation. The animals will be sacrificed 1, 3, 6, 12 and 18 months after implantation for analyses. At each time point, 6 animals will be euthanized for analysis.

Example 2

Preparation of Decellularized Organs

The following method describes a process for removing the entire cellular content of an organ or tissue without destroying the complex three-dimensional infra-structure of the organ or tissue. An organ, e.g. a liver, was surgically removed from a C7 black mouse using standard techniques for tissue removal. The liver was placed in a flask containing a suitable volume of distilled water to cover the isolated liver. A magnetic stir plate and magnetic stirrer were used to rotate the isolated liver in the distilled water at a suitable speed for 24-48 hours at 4° C. This process removes the cellular debris and cell membrane surrounding the isolated liver.

After this first removal step, the distilled water was replaced with a 0.05% ammonium hydroxide solution containing 0.5% Triton X-100. The liver was rotated in this solution for 72 hours at 4° C. using a magnetic stir plate and magnetic stirrer. This alkaline solution solubilized the nuclear and cytoplasmic components of the isolated liver. The detergent Triton X-100, was used to remove the nuclear components of the liver, while the ammonium hydroxide solution was used to lyse the cell membrane and cytoplasmic proteins of the isolated liver.

The isolated liver was then washed with distilled water for 24-48 hours at 4° C. using a magnetic stir plate and magnetic stirrer. After this washing step, removal of cellular components from the isolated was confirmed by histological analysis of a small piece of the liver. If necessary, the isolated kidney was again treated with the ammonium hydroxide solution containing Triton X-100 until the entire cellular content of the isolated liver was removed. After removal of the solubilized components, a collagenous three-dimensional framework in the shape of the isolated liver was produced.

This decellularized liver was equilibrated with 1× phosphate buffer solution (PBS) by rotating the decellularized liver overnight at 4° C. using a magnetic stir plate and magnetic stirrer. After equilibration, the decellularized liver was lyophilized overnight under vacuum. The lyophilized liver was sterilized for 72 hours using ethylene oxide gas. After sterilization, the decellularized liver was either used immediately, or stored at 4° C. or at room temperature until required. Stored organs were equilibrated in the tissue culture medium overnight at 4° C. prior to seeding with cultured cells.

Example 3

Electrospun Matrices

An electrospun matrix was formed using the methods outlined in Example 1. A solution of collagen type I, elastin, and PLGA, were used. The collagen type I, elastin, and PLGA were mixed at a relative concentration by weight of 45% collagen, 40% PLGA, and 15% elastin.

Figure 3:
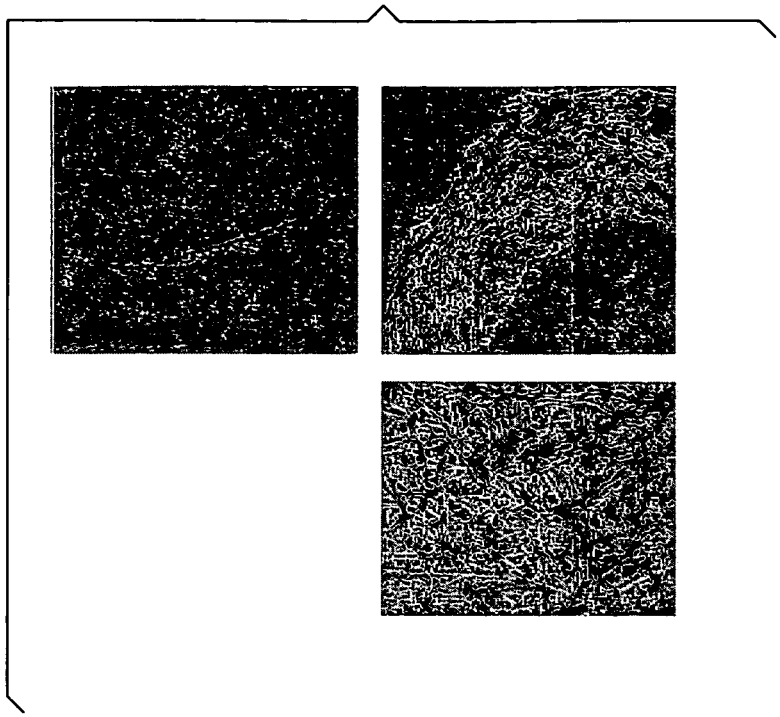
FIG. 3 is an electrospin nanofiber.

The resulting fibrous scaffold had a length of 12 cm with a thickness of 1 mm. A 2 cm representative sample is depicted in FIG. 3. This demonstrates the feasibility of spinning Type I Collagen and elastin into fibers from nanometer to micrometer diameter using concentrations from 3% to 8% by weight in solution. These results also show that by adding PLGA (Mw 110,000) to the mixture, solutions with higher viscosity and improved spinning characteristics could attained. By increasing the solution concentration to 15%, thicker, stronger scaffolds were able to be built while maintaining the collagen and elastin components.

Collagen type I stained positively on the decellularized scaffolds, demonstrating uniform distribution. Elastin distribution within the scaffolds was determined by Movat staining. The electrospun scaffolds with 15% elastin demonstrated a uniform elastin matrix throughout the scaffold wall. These findings indicate that the matrix content and distribution of the electrospun scaffolds can be manipulated to achieve various matrix compositions depending on the need.

Results of biocompatibility assays were calculated as a percentage of negative control and both electrospun scaffolds performed similarly to the decellularized blood vessel. These data suggest that the biocompatibility of electrospun scaffolds is similar to that of decellularized scaffold.

Figure 4:
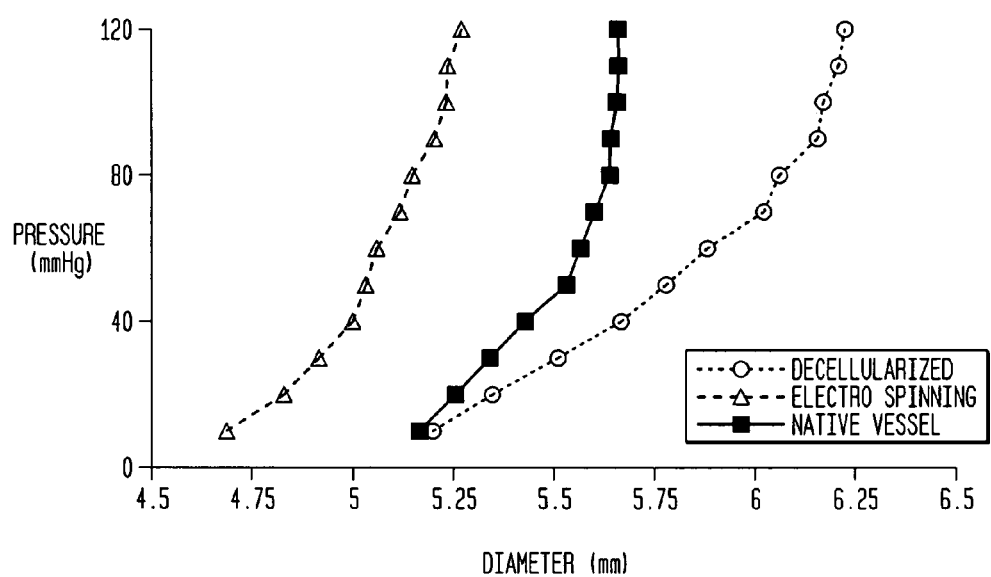
FIG. 4 is graph of pressure-diameter curves of vascular graft scaffolds.

Results of mechanical testing for compliance show a typical pressure-diameter curve for native vessels, as well as for decellularized and electrospun scaffolds. The diameter change was approximately 5% for native vessels and electrospun scaffolds within the physiologic pressure range which is consistent with the in vivo mechanical behavior of porcine and human arteries (FIG. 4). These data demonstrate that the electrospun scaffolds created have a compliance similar to that of a native vessel.

Results of the axial and circumferential mechanical tests from electrospun scaffolds tended to exhibit a more isotropic behavior. Strain in the axial and circumferential directions were nearly equivalent before failure occurred.

The results of burst pressure testing show that the burst pressure for the electrospun construct was 1,425 mmHg or nearly 12 times systolic pressure. These data suggest that electrospun scaffolds have adequate initial strength and elasticity to withstand the mechanical environment when being surgically placed in the circulatory environment.

Histological analysis of the explanted vascular scaffolds from mice showed that there was no evidence of inflammation or tissue encapsulation.

Collectively, these results show that it is possible to control the composition of electrospun scaffolds for use as vascular grafts. Higher concentrations of collagen type I and elastin than previously employed, and mixing with PLGA, result in improved spinning characteristics and strength of grafts, which resist almost 12× systolic pressure. Scaffolds also exhibited compliance characteristics similar to native arteries. Scaffolds had an average fiber diameter of 720 nanometers. EDC crosslinked scaffolds demonstrate superior cell proliferation characteristics to glutaraldehyde crosslinked scaffolds as assessed by mitochondrial metabolic activity assay. Cell viability assays did not demonstrate as pronounced a difference in crosslinking method. These results are some of the first data on biocompatibility of electrospun scaffolds created with biological polymers and PLGA. This work demonstrates the promise of electrospinning as a fabrication process for vascular graft scaffolds.

Example 4

Cross-Linking of Electrospun Matrices

This example demonstrates how to increase the strength and stability of the electrospun scaffold by chemical cross-linking. The scaffolds were soaked in 20% dextran solution in phosphate buffered saline prior to crosslinking to reduce hydration-induced swelling and contraction of the scaffold. The scaffolds were crosslinked by immersion in EDC/NHS in MES/EtOH solution for 2 hours at room temperature. Scanning electron micrographs of the resulting fibers showed fiber diameters of 500 nm or less and a random orientation of fibers. Atomic force microscopy of the scaffold and a confocal image of nanofibers with an adhering endothelial cell demonstrate the scaffold structure. These data show that it is possible to fabricate vascular scaffolds from biological polymers with mechanics and structure similar to decellularized scaffolds and native arteries.

Example 5

Distribution of Collagen and Elastin Content

The relative quantity and distribution of collagen and elastin in a vascular scaffold is important to the mechanical properties and function of the seeded graft. The scaffold composition was assessed using histochemical analysis for collagen types I, II, and III, elastin and hematoxylin, and eosin (H&E) staining was also performed.

The levels of collagen type I, II, and III, and elastin for decellularized matrices and collagen type I and elastin for electrospun matrices were analyzed using computerized histomorphometric analysis. NIH Image/J Image analysis software (National Institutes of Health, Bethesda, Md.) was used for the analysis.

Immunohistochemical analyses using antibodies specific to collagen types I, II and III were performed on the decellularized and electrospun scaffolds. The decellularized scaffolds showed similar collagen type I and III in the vascular media, which corresponds to normal blood vessels. In this study, 45% collagen type I was used to demonstrate the controllability of the scaffold fabrication. Collagen type I stained positively on the decellularized scaffolds, however, collagen type III stained negatively. Elastin distribution within the scaffolds was determined by Movat staining. Abundant elastin fibers were observed in the entire decellularized scaffold wall with a prominent distribution in the serosal and luminal surface. The electrospun scaffolds with 15% elastin demonstrated a uniform elastin matrix throughout the scaffold wall. These findings indicate that decellularized vascular scaffolds possess matrices similar to normal vessels and that the matrix content and distribution of the electrospun scaffolds can be manipulated to achieve various matrix compositions depending on the need.

Histograms of the distribution of color were used to determine relative amounts of each component from each stain against negative controls. All values were normalized by area for comparison. Amounts of collagen I, elastin, and PLGA were known for electrospun matrices because of fabrication parameters. Calibrating the image data for relative amounts of collagen utilized both the normalized areas with negative controls, and was calibrated based on known composition of electrospun matrices.

The results demonstrate the composition of collagen I, II, and III, and elastin, in the decellularized scaffolds as well as component percentages in electrospun matrices. These studies show that the collagen and elastin content of decellularized and electrospun scaffolds is similar to that of native vessels.

Example 6

Compliance Testing of Scaffolds

Compliance mismatch is one of the most common causes of vascular graft failure, resulting in intimal hyperplasia and occlusion. If the scaffold is too compliant, it may form an aneurysm. This example describes how to test for compliance of the scaffolds. Decellularized and electrospun vessel shaped scaffolds were immersed in a water bath and cannulated at either end. One cannula was connected to a column of water and the other to a drainage tube. The column of water was high enough to create a pressure within the vesselshaped scaffold of 120 mmHg. Water was drained through the scaffold in order to lower the pressure in increments of 10 mmHg. At each increment, the diameter of the scaffold was recorded using a digital camera. This process was repeated until the pressure was 0 mmHg. Results show the typical pressure-diameter curve for native vessels, and the experimental curves for decellularized and electrospun scaffolds. The diameter change was approximately 5% for native and electrospun and 15% for decellularized scaffolds within the physiologic pressure range which is consistent with the in vivo mechanical behavior of porcine and human arteries. Thus, both decellularized and electrospun scaffolds have a compliance similar to that of a native vessel.

Example 7

Circumferential and Axial Loading of Decellularized and Electrospun Vessels

Figure 5A:
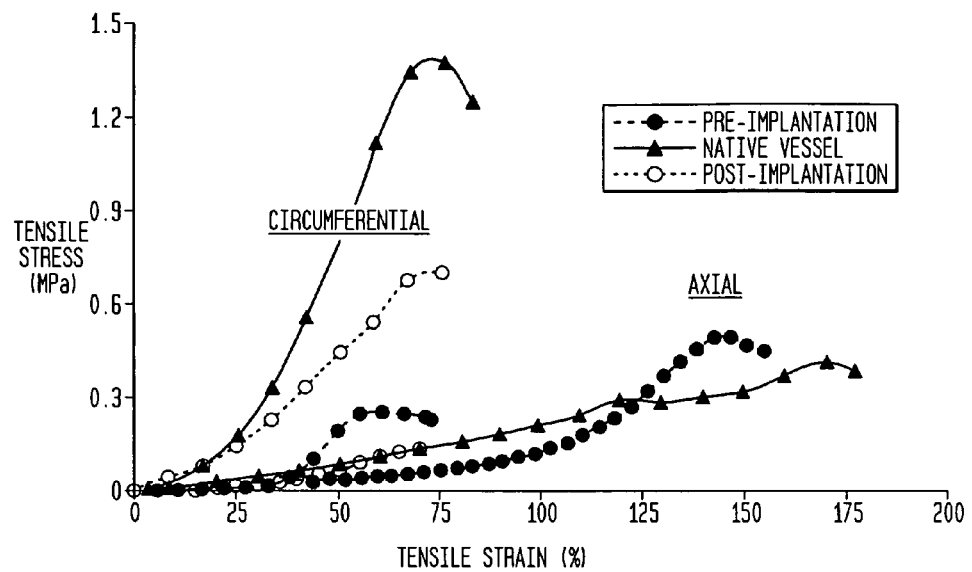
FIG. 5A is a graph of axial and circumferential stress-strain data from uniaxial testing of two decellularized constructs.
Figure 5B:
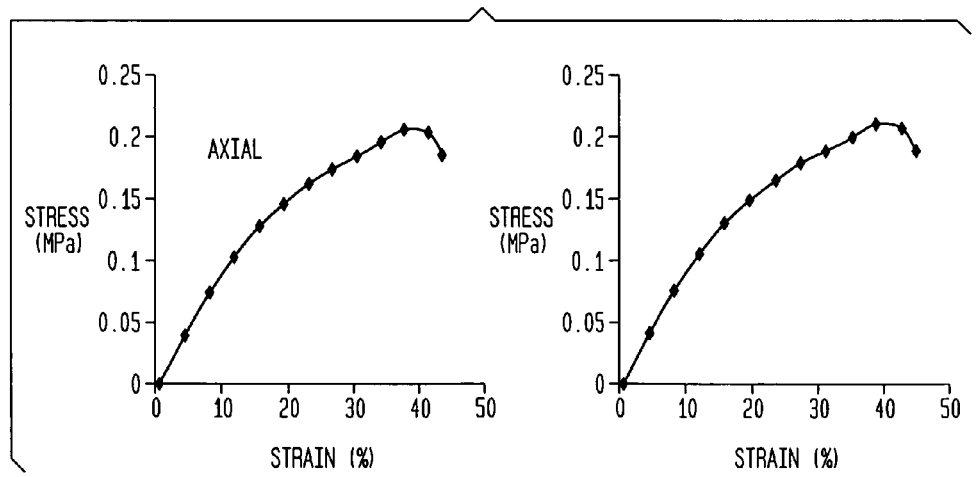
FIG. 5B is a graph of axial and circumferential stress-strain data from uniaxial testing of an electrospun vessel.

Vessels must resist higher stress in the circumferential direction than in the axial direction. Native vessels adapt their mechanics to this loading environment. It is important that the decellularized and electrospun scaffolds exhibit a mechanical behavior similar to native vessels. Thus, mechanical loading tests were performed on the decellularized vessels and electrospun vessels in the axial and circumferential directions using a uniaxial load test machine (Instron Corporation, Issaquah, Wash.). An entire vessel-shaped scaffold was clamped at its cut ends for the axial test. The crosshead speed was set at 0.5 mm/sec and the test was stopped when the strain decreased by 10% after the onset of failure. For testing in the circumferential direction, a ring of material was cut from the scaffold, opened into a strip and then clamped at either end of the strip. This test was also performed at a rate of 0.5 mm/sec. Results of the axial and circumferential mechanical tests from electrospun scaffolds are shown in FIGS. 5A and 5B, respectively.

The electrospun scaffolds tended to exhibit a more isotropic behavior. Strain in the axial and circumferential directions were nearly equivalent before failure occurred. In general, the decellularized construct exhibits the orthotropic mechanical behavior that is expected from the known mechanical behavior of arteries. In particular, strain in the circumferential direction is lower than strain in the axial direction. This was true for scaffolds prior to and after implantation.

The burst pressure for vascular scaffolds was found by monitoring increasing pressures within the vessel until failure occurred. A pressure catheter was inserted through a cannulating fixture at one end of the vessel. A 60 cc pressure syringe was inserted through a custom cannula at the other end of the vessel. The pressure was increased until failure or leakage occurred and the pressure change was recorded. The results show that the burst pressure for the decellularized construct was 1,960 mm Hg or approximately 16 times systolic pressure. The burst pressure for the electrospun construct was 1,425 mm Hg or nearly 12 times systolic pressure. We demonstrated that both electrospun and decellularized scaffolds had adequate strength and elasticity and may be substitutes for native vessels.

Example 8

Isolation, Characterization and Vessel Seeding of Sheep Progenitor EPC and MPC

Progenitor EPC and progenitor muscle cells (MPC) were isolated from 60 ml peripheral blood of the internal jugular vein of sheep. The Lleukocyte fraction was obtained by centrifuging on a Histopaque density gradient. Some of the cells were resuspended in medium and plated on fibronectin coated plates. At 24 hr intervals the floating cells were transferred to new fibronectin coated plates. EPC were induced by growth in EGM-2 medium that contained VEGF and bFGF. The rest of the cells were cultured in the presence of 10 µM 5-Azacytidin for 24 hours. Thereafter floating cells were transferred to a new fibronectin coated plate and cultured in myogenic medium (DMEM low glucose containing 20% fetal bovine serum, 10% Horse Serum, 1% Chick Embryo extract and 1% antibiotics) in order to induce MPC. EPC and MPC were cultured for 4-6 weeks in order to assume differentiated morphology. Immunohistochemical analysis of EPC showed that most of the cells expressed VE cadherin and CD31 but not Desmin. However, MPC showed expression of Vimentin and Desmin but not of VE cadherin. The expression of these markers was maintained during culture in vitro. These results indicate that cultured EPC and MPC possess EC and muscle cell phenotype, respectively.

EPC were labeled by PKH 26 green fluorescent dye and MPC were labeled by PKH 27 red fluorescent dye. Labeled EPC and MPC were seeded on the luminal and the outer surfaces of decellularized vessel segments, respectively, in order to demonstrate the biocompatibility of the decellularized vessel. After 7 days the presence of red and green labeled cells on the decellularized vessel was noted. In addition, seeded vessels were seeded with a suspension of red-labeled MPC and green labeled-EPC ($5 \times 10^6$ cells/ml) and cells were allowed to grow for 7 days. The vessels were embedded in OCT media in order to obtain frozen sections. The sections were stained with DAPI. To detect cell nuclei, sections were visualized using a fluorescent microscope. Data shows that EPC were maintained on the luminal side of the scaffold and MPC on the serosal surface.

Example 9

Cell Attachment

A confluent monolayer of endothelial cells is the most important barrier against thrombosis formation. Endothelial cell mediated NO production is important in maintaining the vascular tone. To examine cell attachment, the decellularized and electrospun vessels were seeded with endothelial cells. Cell attachment was assessed using scanning electron microscopy of scaffolds seeded with a mouse endothelial cell line (MS1). SEM micrographs reveal a confluent monolayer on the inner surface of both the decellularized and electrospun vessels at 48 hours. These results indicate that endothelial cells form confluent monolayers on decellularized and electrospun scaffolds.

Example 10

Biocompatibility (Cell Viability and Proliferation)

Long-term viability of cells is necessary for the seeded scaffold to remodel itself into a viable, patent vessel. To test for cell viability, decellularized and electrospun constructs were placed in 24-well plates with approximately 100 mg of material per well. Four different types of material were tested for biocompatibility and cell survival, with one negative control well with no material: (1) GA-NFS (1% glutaraldehyde crosslinked electrospun scaffold); (2) EDC-NFS (EDC-crosslinked electrospun scaffold); (3) nBV (natural blood vessel, decellularized); (4) Latex (latex rubber, positive control).

Figure 6A:
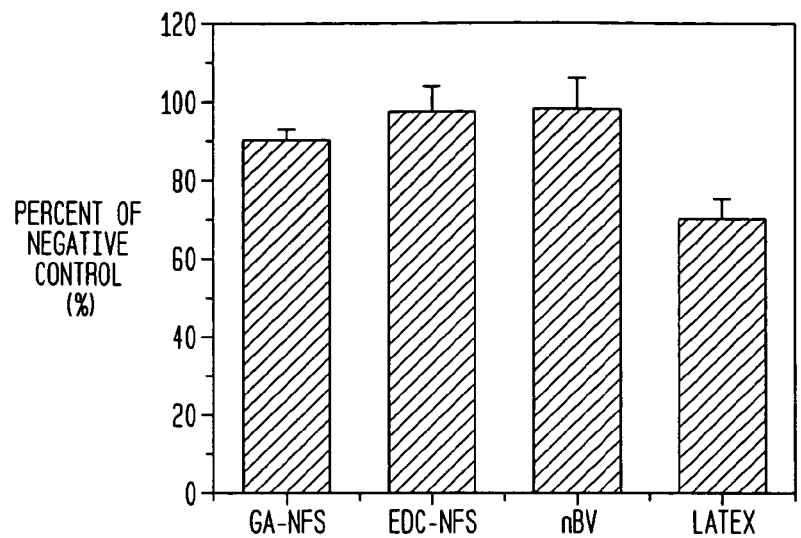
FIG. 6A is a graph of cell viability of endothelial cells cultured on four matrices.

Endothelial cells were seeded in the wells on a scaffold for testing via the direct contact method. For cell viability, cell layers were rinsed with PBS. 0.005% w/v neutral red was added in culture medium. The neutral red solution was removed after 4 hours incubation at 37° C. with 1% acetic acid and 50% ethanol solution by volume was added for dye extraction, and dye extraction was shaken for 5 minutes. Absorbance was then measured at 540 nm using a spectrophotometer. The intensity of red color obtained was directly proportional to the viability of the cells and inversely proportional to the toxicity of the material. Results were reported as a percentage of negative control, and both electrospun scaffolds performed similarly to the decellularized blood vessel (FIG. 6A).

Figure 6B:
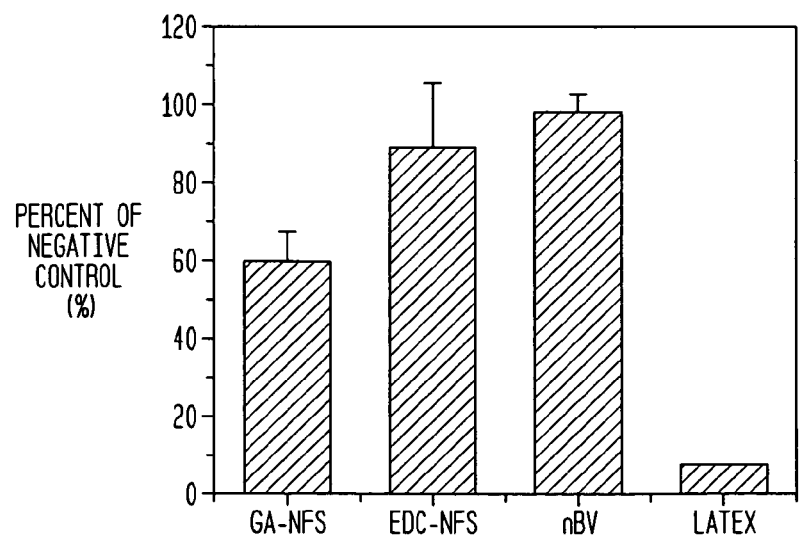
FIG. 6B is a graph of mitochondrial metabolic activity of endothelial cells cultured on four matrices.

Cell proliferation was tested using the mitochondrial metabolic activity assay. Cell layers were first rinsed with PBS. MTT solution was added at 1 mg/mL in PBS containing 1 mg/mL glucose. MTT solution was removed after 4 hours incubation at 37° C. Dimethyl sulfoxide (DMSO) was used to dissolve insoluble formazan crystals, and the absorbance at 540 spectrophotometer. The intensity of blue color was directly proportional to the metabolic activity of the cell populations and inversely proportional to the toxicity of the material or extract. The gluataraldehyde treated matrices show more pronounced differences than in proliferation assays, with EDC treated scaffolds being similar to natural blood vessels (FIG. 6B).

Figure 7A:
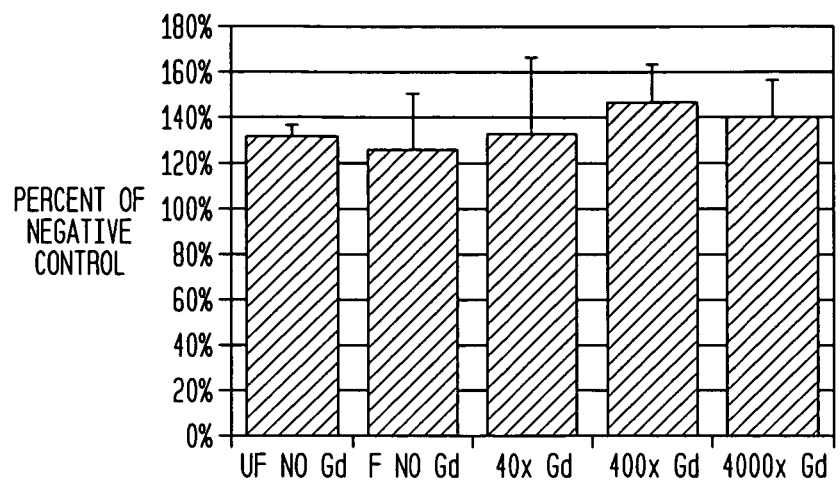
FIG. 7A is a graph of cell viability of endothelial cells cultured on five matrices.
Figure 7B:
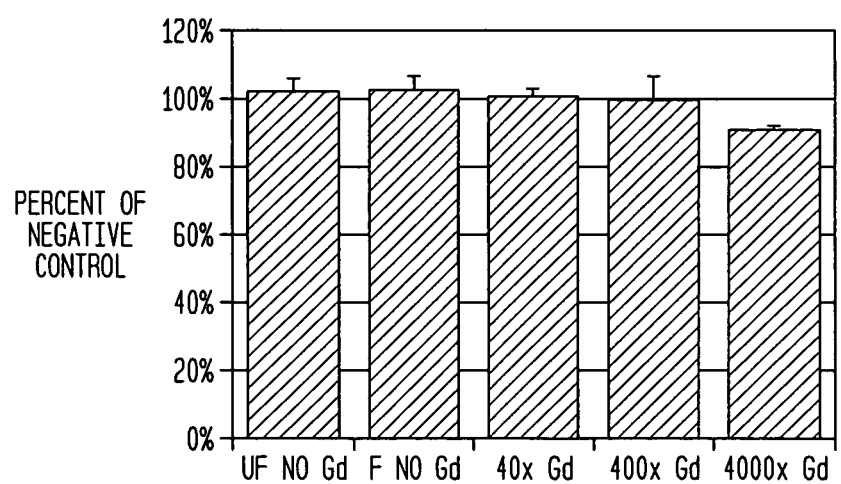
FIG. 7B is a graph of mitochondrial metabolic activity of endothelial cells cultured on five matrices.

Cell viability and proliferation testing was also performed to determine the effects of various concentrations of gadolinium (Gd) on the scaffolds, on cell survival (FIG. 7). The tests revealed little effect of Gd levels on cell viability or survival. The results indicate that both scaffolds can promote cell growth and thus may be used for the bioengineering of vascular grafts.

Example 11

External Functionalization of Matrices

This example describes how to generate matrices with image enhancing agents and quantum dots. In particular, Gd-DPTA and quantum dot functionalization of an external scaffold. The scaffold can be any biocompatible substrate, such as a synthetic PGA matrix, an electrospun matrix, or a decellularized matrix. At present, no clinically available vascular graft allows for noninvasive monitoring of the integration of the graft in vivo, nor does any graft incorporate anticoagulants into its structure. A reliable method is needed to attach nanomaterials to scaffolds, e.g., vascular scaffolds, in order to increase functionality, in particular as a material marker and for anticoagulation. Carboxylated Gd and quantum dot (QD) materials were coupled to the surface of both the decellularized and the electrospun scaffolds using an EDC/sulfo-NHS method. Any unreacted material was quenched and removed by rinsing the scaffold with 0.1 M Tris buffer. The liquid from the final washing was colorless under UV elimination.

Under blacklight illumination the functionalized scaffold shows multicolor fluorescence. Areas of red-orange emission are from the quantum dots. The pale white color, which is stronger in intensity than the control tissue, comes from the Gd containing material that can fluoresce with a pale blue color. The data shows that it is possible to incorporate heparin onto the surface of a scaffold. The scaffolds are also able to bind Gd.

Example 12

Internal Functionalization of Matrices

This example describes the production of electrospun matrices with image enhancing agents and therapeutic agents. In particular, Gd-DPTA and QD addition to the internal electrospun scaffolds. Fabricating vascular scaffolds using electrospinning provides an opportunity to incorporate image enhancing agents within the bulk material. Solutions were spun successfully containing gadolinium diethylenetriamine pentacetic acid (Gd-DPTA) in HFP at a concentration of 15 mg/mL and with quantum dots added at a concentration of 8% by volume from a quantum dot solution of 25.5 nmol/mL in toluene. No morphological change was noted in the scaffolds due to the addition of the Gd-DPTA or the QDs. These results show that incorporating nanoparticles into the scaffolds has only a minimal effect on the morphology of the resulting structure.

Example 13

Matrices with Quantum Dots

This example describes how to couple therapeutic agents, such as heparin to the quantum dots (QD). Heparin is a potent anticoagulant agent. To avoid systemic administration, a method is needed to control the release of heparin from the vascular scaffold and to bind the heparin to the scaffold. In this experiment, EDC (10 mg) and sulfo-NHS (2 mg) was added into the 5 mL (0.05 mg/mL) of carboxylated quantum dots in aqueous solution under gentle stirring for 1 hr at room temperature. EDC activated heparin (30 mg) was prepared according to the same EDC and NHS method as described above. In order to conjugate quantum dots and heparin, 5 mg phenylene diamine (PDA) was added to the activated quantum dots and heparin solutions while stirring for 2 hr at room temperature. The quantum dot-heparin (QD-heparin) conjugation can be quenched by adding an equal volume of 1 M Tris buffer solution (pH 7.4) and stored in 4° C.

Microencapsulation of QD-heparin was performed by double emersion. Briefly, 4 mL of internal aqueous phase containing 30 mg QD-heparin conjugation and 10 mg bovine serum albumin emulsified in 8 mL of a solution of 100 mg PLGA (MW; 110,000) and 100 mg PCL (MW; 110,000) in DCM. The solution was emulsified by vortexing for 5 min at room temperature. This W/O dispersion was diluted into 200 mL of 1% (w/v) aqueous PVA solution under stirring for 4 hr at room temperature. The microcapsules (MCs) were washed several times with deionized water and then lyophilized overnight. QD-heparin nanocapsules (NC) were incorporated into scaffolds by placing the functionalized vascular scaffold in 1 wt % PLL in PBS. Vascular scaffolds were immersed in the PLL-nanocapsule solution for 3-4 hours, and lyophilized before sterilization with gamma irradiation.

A fluorescence image of an isolated microcapsule containing quantum dots shows that the characteristic fluorescence from the quantum dots used in this experiment is at 500 nm. The data show that it is possible to bind heparin to quantum dots and encapsulate the bound heparin in a biodegradable polymer, for attachment to the vascular scaffold.

Example 14

Release Kinetics of Heparin: In Vitro Release of Heparin and Burst Release by Irradiation To assess the effectiveness of quantum dots for controlled delivery of heparin, the release kinetics of the drug was analyzed following an irradiation burst. In order to evaluate the burst release of heparin, 0.55 mg of PLGA microcapsules with QD-heparin were suspended in 2 ml of buffered saline solution. The solutions were irradiated for 0.0, 10, and 30 min using an AM1.5 solar simulator at 75 mW/cm$^2$. On days 1, 3, and 5 the samples were then cooled to 4° C. and centrifuged at 4500 rpm for 20 min. The solutions were filtered (0.45 m pore size) to remove any microcapsules for the optical measurements.

Figure 8A:
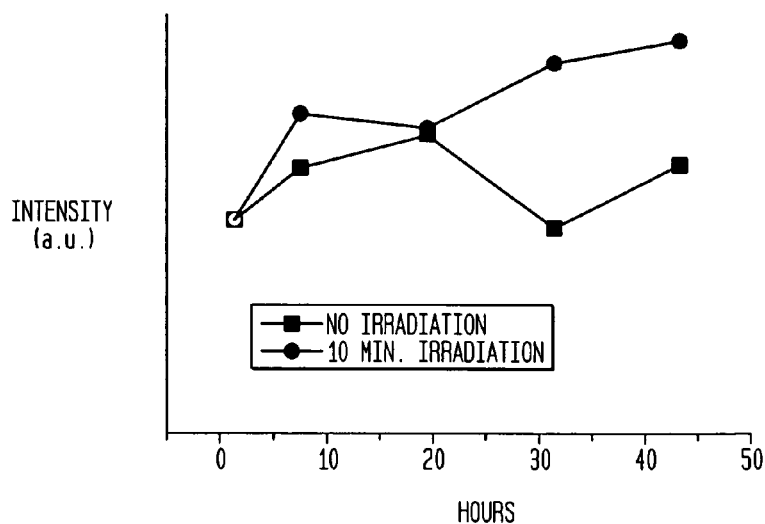
FIG. 8 is a graph of microcapsules containing heparin which show heparin release upon near infra-red irradiation.
Figure 8B:
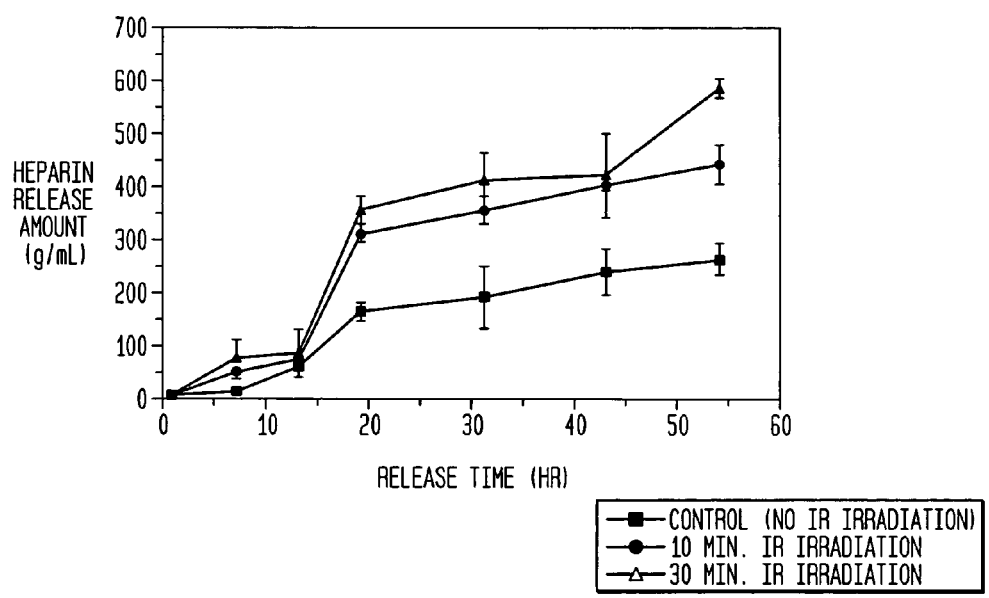

Luminescence measurements were performed using an argon ion laser (514.5 nm at 400 mW/cm$^2$) as the excitation source and spectra were collected using a CCD spectrophotometer with an integration time of 40 sec. Irradiated samples showed increased luminescence over time indicating a "burst effect". The kinetic profile of heparin confirms that irradiation induced the burst release out of functionalized microcapsules. Heparin release was monitored by optical analysis (FIG. 8A) and biochemical analysis (FIG. 8B). These results indicate that NIR can be used to initiate the release of heparin from the QD-heparin microcapsules.

Normally, heparin is administered at the site of implantation immediately following surgery to prevent acute thrombosis. Afterwards, heparin is administered within the first week twice a day by injection. In order to improve the patient's compliance, heparin could be immobilized in vascular scaffolds for extended period of time. However, the immobilization of heparin to the scaffolds results in a slow release of heparin which is not appropriate for thrombus prevention. To accelerate the burst release of heparin, near infrared (NIR) irradiation of the quantum dots bound to heparin can to be used to achieve this goal.

Example 15

Determination of the Remaining Heparin in Retrieved Vessel Implants from Mice

Figure 9:
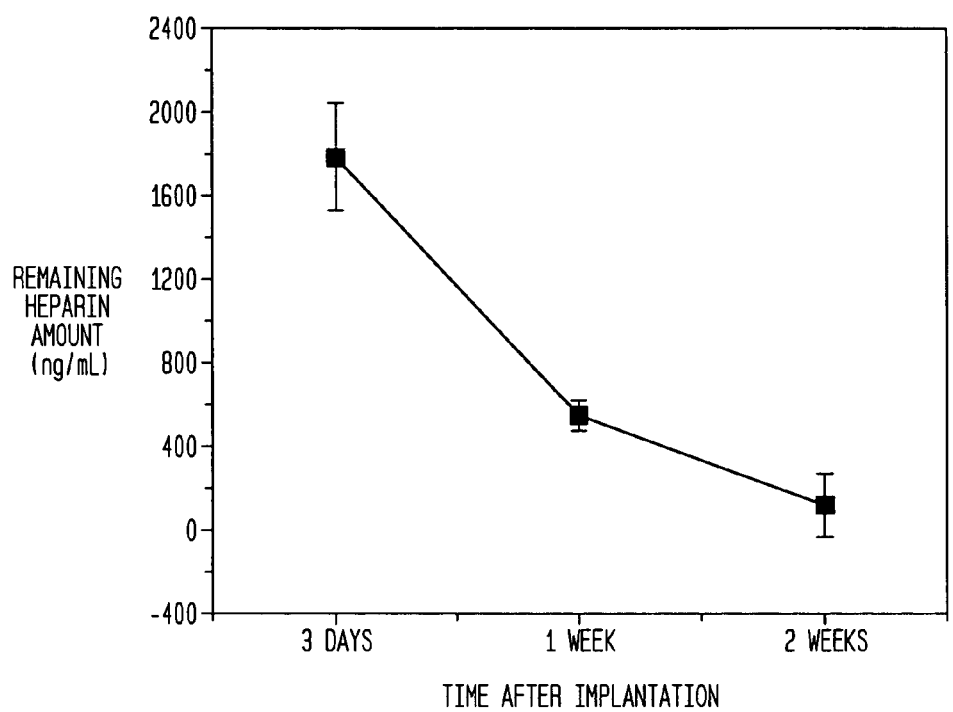
FIG. 9 is a graph showing the quantification of remaining heparin from retrieved vascular scaffolds.

To assess the effectiveness of heparin in an in vivo model, heparin must be evaluated after the explantation of the scaffold. The remaining heparin in functionalized blood vessels (heparin-QD) implanted in mice was determined by toluidine blue staining and most of the heparin is shown to have diffused out of the vessel two weeks after implantation. The heparin content was analyzed by a Rotachrome kit and the data confirms that very little heparin remains after two weeks. The data show that the activity of heparin was successfully prolonged in the scaffold beyond its normal 1-2 hour half-life (FIG. 9).

The inflammatory response of quantum dots should be addressed for clinical applications. From the histological analysis of the explanted vascular scaffolds from mice, there was no evidence of inflammation or tissue encapsulation. The data indicate that conjugated heparin had only a minimal inflammatory response.

Example 16

Evaluation of the Anti-Thrombogenic Properties of Heparin Immobilized Vessels

Although heparin is a powerful anticoagulant, it was important to verify that this property still exists after immobilization. Two methods of heparin binding were tested. Thirty milligrams of heparin was incubated in 20 mM EDC and 10 mM sulfo-NHS in PBS for 2 hours at room temperature, and a 3 mm diameter decellularized scaffold was then immersed in heparin-EDC solution for 2 hours at room temperature. After cross-linking, the sample was rinsed in PBS several times to completely remove residual EDC. Subsequently immobilization of heparin by physical adsorption was performed using Poly(L-lysine) (PLL): The 3 mm diameter decellularized scaffold was incubated in 2 mg/mL PLL solution for 2 hours at room temperature. The PLL-adsorbed scaffold was immersed in 15 mg/mL heparin solution for 1 hour at room temperature. The anti-thrombogenic property of each method was evaluated using whole blood from sheep by toluidine blue staining. Immediate coagulation was observed from the decellularized scaffold while no significant sign of coagulation was found from both EDC and PLL reacted decellularized scaffolds 36 hours after blood treatment. The heparin-PLL decellularized scaffold demonstrated the weakest staining which indicated the highest loading of heparin in the scaffold. These results showed that immobilized heparin was effective in preventing thrombus.

Example 17

Enhanced MRI Imaging

This example demonstrates the improved imaging observed with gadolinium. In vitro experiments were conducted on cell scaffolds with gadolinium to determine the improvement in magnetic resonance imaging. Cylindrical cell scaffolds 20 millimeters long with an internal radius of 10 millimeters and a outer radius of 14 millimeters were created with different Gd loading concentrations. Cell scaffolds were individually placed in test tubes and submerged in PBS. The four test tubes were arranged left to right in the following order: non-functionalized cell scaffold (control 1), functionalized scaffold (control 2), 1×Gd concentration cell scaffold, 100×Gd concentration (control 3) and a 1000×Gd concentration cell scaffold. (100× designates a concentration in solution during functionalization of 55 mg/kg of Gd-DPTA) Axial T1 weighted spin echo images were acquired on a on a GE Healthcare Technologies magnetic resonance imaging (MRI) 1.5T TwinSpeed scanner.

The T1 weighted image acquired with a phased array coil and a 200 millisecond repetition time (TR) was obtained. Additional imaging parameters are as follows: echo time (TE)=13 ms, slice thickness=0.8 mm, 256×128, field of view (FOV)=12 cm×6 cm, number of averages=100, and phase direction was right to left. The cell scaffolding loaded with 1000×Gd (right most test tube) is clearly visible compared to controls 1, 2, and 3. Samples were washed twice with TRIS buffer and PBS and stored in PBS for 2 weeks prior to imaging.

The previously described experiment was repeated for two different Gd loaded scaffold preparations: surface and volume loading. The scaffold on the left is a cylindrically shaped scaffold identical to the previously described experiment with a surface loaded 1000×Gd preparation. The scaffold on the right is a planar sheet of scaffold with the Gd embedded throughout the electrospun fibers as described previously. The scaffold that had the Gd electrospun into the fiber showed a much higher contrast. The normalized signal intensities of the scaffold for the surface preparation and volume preparation are 1.5±0.2 and 2.98±0.35, respectively. The data on MRI Imaging of Gd loaded scaffolds showed that Gd increases MRI contrast in proportion to the level of Gd loaded in the scaffold.

Example 18

In Vivo Preliminary Data on Rodents

Although Gd may be maintained in the scaffolds in vitro, it is necessary to demonstrate that it retains functionality in vivo. This experiment investigates the in vivo functionality of the scaffolds. Electrospun vascular scaffolds were implanted subcutaneously in a mouse for two weeks prior to imaging. Gd was added to one of the vascular scaffolds to enhance its contrast on a T1 weighted image. A sagittal localizer image was acquired from the mouse and a T1 weighted coronal image containing the two scaffolds was prescribed off the sagittal image. The important imaging parameters of the T1 weighted image are repetition time (TR) 300 milliseconds, echo time (TE) 14 milliseconds, and slice thickness 2 millimeters. A 50% improvement in image contrast of the Gd scaffold compared to the control. These results in a rodent model demonstrate that the characteristics seen in vitro are maintained in vivo.

Example 19

Ex Vivo Preliminary Data on Sheep Engineered Vessels

In vivo results in the rodent model were limited to subcutaneous specimens. It was necessary to demonstrate similar results in a scaffold exposed to blood flow in a large animal model. To determine the feasibility of using the cell seeded scaffolds containing the nanoparticles (heparin conjugated with quantum dots and Gd-DTPA), femoral artery bypass procedures were performed in sheep. Peripheral blood samples were collected, circulating progenitor cells were selected and differentiated into endothelial and smooth muscle cells in culture. Each cell type was grown, expanded separately and seeded on decellularized vascular scaffolds containing the nanoparticles (30 mm long). Nanoparticle containing scaffolds without cells served as a control. Under general anesthesia, sheep femoral arteries were imaged with duplex ultrasonography (B-mode ultrasound and Doppler spectral analysis) with a high resolution 15 MHz probe (HDI-5000, ATL) prior to scaffold implantation. The femoral artery was exposed through a longitudinal incision over a length of 6 to 8 cm. Aspirin and heparin were used as anticoagulation and the femoral artery was clamped and divided proximally. An end-to-side anastomosis was created between native and engineered artery. The distal anastomosis was created in a similar fashion and blood flow restored through the implant followed by ligation of native femoral artery between the two anastomoses. Doppler ultrasonography was performed using a sterile probe to establish scaffold dimensions and blood flow after implantation. Wounds were closed and the animals recovered from anesthesia prior to 3500 return to standard housing. Aspirin was administered routinely for 7 days orally for anticoagulation.

Duplex ultrasound imaging was performed to determine the presence of thrombosis, lumen narrowing intimal hyperplasia and graft wall stricture, and graft aneurismal degeneration. Longitudinal and cross-sectional images of the pre- and post operative arterial segments showed a patent lumen 0 with similar peak systolic, end-diastolic and time averaged velocities as the normal artery. The arterial wall thickness and luminal diameter of the engineered bypass was similar to native artery. The engineered arterial bypass and the contralateral normal femoral artery were scanned with MRI. T1 weighted spin echo MR images were acquired with the following parameters: 256×126 matrix, 12×6 mm FOV, 400 ms TR, 13 ms TE, 1 mm slice thickness, and 50 excitations. Average signal intensities of the samples were normalized by the background water intensity to account for receiver coil nonuniformities. The normalized intensities were 2.62 and 2.10 for the scaffold and normal vessel, respectively.

This experiment was repeated at several different TRs and the signal intensity measured for the scaffold and the normal vessels. As expected, the signal intensity for the gadolinium enhanced scaffold is always greater than the normal vessel. These results confirmed that Gd and heparin loaded decellularized scaffolds maintain patency in a sheep model and maintain MRI contrast.

Gadolinium is a MR contrast agent that enhances images primarily by decreasing the spin-lattice relaxation time (T1) of protons in tissues. Unlike radionuclides, it will remain effective as long as it is localized in the engineered vessel. These results shown in vitro through repeated rinsing of the Gd doped scaffolds and in vivo through imaging of the engineered vessel, that the functionalized Gd nanoparticles are stable in the matrix. Within the first 3 months, approximately 80% of the graft will be remodeled. The Gd localized in the matrix will initially enhance the imaging of the graft. The change in MR signal over time, as the concentration of Gd decreases with remodeling of the vascular graft, will allow us to quantify the remodeling rates.

Example 20

Histomorphological Characteristics of Bypass Grafts in Sheep

To demonstrate cell attachment on the retrieved engineered vessels initially seeded with endothelial and muscle cells, scanning electron microscopy was performed 2 weeks after implantation. The implanted decellularized scaffolds seeded with cells showed a uniform cell attachment on the luminal surface of the engineered artery similar to normal vessels. The scaffolds without cells failed to exhibit cell attachment. These observations indicate that the cells seeded on decellularized vascular scaffolds are able to survive and remain attached after surgery.

To assess the histo-morphological characteristics of the retrieved tissue from engineered arterial bypass grafts in sheep, histological evaluation was performed. The engineered arterial specimens were fixed, processed and stained with hematoxylin and eosin (H&E) and Movat staining. The cell seeded engineered grafts contained uniform cellularity throughout the vascular walls. Abundant elastin fibers were observed in the entire arterial wall with a prominent distribution in the serosa and luminal surface. These findings demonstrate that the engineered vessels, seeded with peripheral blood derived progenitor cells differentiated into endothelial and smooth muscle cells, are able to show an adequate cellular architecture similar to native vessels.

Collectively, these studies show that it is possible to fabricate and functionalize both decellularized and electrospun scaffolds with cells (endothelial and smooth muscle) and nanomaterials (quantum dot—conjugated heparin) that are known to have a positive therapeutic benefit. Moreover, the data shows the successful incorporation of molecules (gadolinium) enhancing MRI contrast to monitor the engineered vessels over time. The combination of functionalization and imaging offers the potential for making these scaffolds an ideal vascular substitute. The matrices are biocompatible, possess the ideal physical and structural properties, and have been shown to be functional for over 4 months in the carotid artery of sheep.

Example 21

To Characterize the Engineered Vascular Grafts

In order for a vessel to function normally, it should have the appropriate structural properties to accommodate intermittent volume changes. In pathologic conditions, normal vessel function and mechanical properties may be compromised. To translate the use of bioengineered vessels to patients, it is first necessary to confirm that normal vessels are being formed, and that they retain adequate phenotypic and functional characteristics over time, especially with growth.

(i) Mechanical Testing

Understanding the mechanical properties of explanted vessels provides information about the adaptive remodeling those vessels have undergone while in the host animal. Mechanical testing will include arterial elongation (axial and circumferential), compliance, burst pressure, stress relaxation, and creep.

(ii) Phenotypic and Composition Analyses

Histological and immunohistochemical analysis can be performed on the retrieved vascular grafts. Longitudinal and cross sections will be taken from the transition zones between native vessels and graft and from the rest of the graft. Specimens will be fixed, processed and stained with Hematoxylin and eosin (H&E) and Masson's trichrome. Cross-sectional areas of the adventitia, media, intima and lumen will be measured using computer-assisted analysis of digital images (NIH Image Software). In addition to cross-sectional analysis of the engineered artery body, a separate analysis will be performed for the anastomoses region between native and engineered arteries. The proximal and distal anastomoses will be fixed in formalin, embedded in paraffin, and then cut in cross-section for analysis of lumen caliber and artery wall thickening in step-sections spanning each anastomosis. In parallel, quantitation of thrombus formation will be performed using H&E staining. The phenotypic characteristics of the retrieved tissues will be determined over time.

To determine the degree of endothelial and smooth muscle content of the bioengineered vessels over time, in comparison to normal tissues, multiple molecular markers will be probed immunocytochemically and with Western blot analyses, as described above. These markers will include Anti-Desmin and Anti-Alpha Smooth Muscle Actin, which specifically detects smooth muscle cells. Endothelialization will be evaluated by anti-von-Willebrand factor anti-CD-31 and anti-VEGF receptor, KDR, antibodies, which stain EC specifically. Cell proliferation and apoptosis in engineered arteries will be determined by BrdU incorporation and TUNEL staining.

The composition and distribution of extracellular matrix components, such as collagen and elastin, are important for the normal function of blood vessels. While the collagen network is responsible for tensile strength, elastin is important for the elastic recovery of the vessel. Therefore, an assessment of the collagen and elastin content and distribution of the retrieved tissues over time will be performed with histological and quantitative biochemical assays. To determine whether the retrieved vessels possess normal concentrations of collagen and elastin, as compared to normal controls, the total collagen and elastin content per unit wet weight of the retrieved tissue samples will be measured quantitatively using the Sircol collagen and the Fastin elastin assay systems (Accurate Chemical & Scientific Corporation, Westbury, N.Y.). To determine the anatomical distribution of collagen within the engineered vessels, as compared to controls, Immunocytochemical localization of collagen types I, II and III will be performed using specific monoclonal antibodies (Southern Biotechnology Associates, Inc., Birmingham, Ala.) and with the elastin-specific stain, Movat.

(iii). Physiological Analysis

The ability to synthesize vasoactive agents such as Nitric Oxide (NO) will further determine the functionality of the engineered vascular scaffolds. There is increasing evidence on the importance of NO in vascular hemostasis. NO contributes to resting vascular tone, impairs platelet activation, and prevents leukocyte adhesion to the endothelium.

Briefly, guinea pig thoracic aorta will be harvested, the endothelium layer removed by gentle rubbing and cut into 5-mm segments. Each segment will be suspended between 2 tungsten stirrups for measurement of isometric tension. The vessel segments placed in an organ chamber with 10 ml Kreb's buffer solution at 37° C. with a mixture of 5% $CO_2$, 15% $O_2$ and a balance of N2. Each vessel (2-3 cm in length) is tied to a 21 G needle, which was attached to plastic IV tubing and placed above the organ chamber with the fresh aortic segment. The segments will be contracted with 80 mM KCl Kreb's buffer in a stepwise fashion to obtain a resting tension of 4 g. After resting for 90 minutes, the segments are contracted in response to prostaglandin F2α up to a final concentration of $10^{-7}$M and until a stable contraction of approximately 50% of maximum KCl-induced contraction is achieved. Vasoactive agents and antagonists are then added using an infusion pump through the vessels to induce NO production. Doses of the vasoactive agents between $10^{-7}$-$10^{-3}$ M will be tested and dose-response curves will be constructed.

Example 22

Creating an Artificial Digit

To demonstrate that a small limb can be restored in situ with multiple tissue types, culture expanded bovine muscle progenitor cells (MPC) and osteoblasts or chondrocytes were seeded on their respective region of composite scaffolds to engineer tissue in vivo. The cell seeded scaffolds ("construct"), was implanted in the subcutaneous space of athymic mice. The constructs maintained their volume and initial structure when retrieved 2 months later. Grossly, the engineered composite tissues formed rigid, cartilaginous or bony tissues that were attached to the soft muscle tissue. Histochemistry, immunohistochemistry, and Western blots of the retrieved tissue with their specific markers confirmed muscle, cartilage, and bone formation.

To determine whether the engineered composite tissues possess adequate structural and functional characteristics for their use in the restoration of limb tissue, the explanted composite tissues underwent mechanical and physiological testing. The compression-relaxation analysis of the engineered cartilage tissues demonstrated preservation of structural integrity and resisted high compressive pressures.

Physiological organ bath studies of the retrieved muscle tissues demonstrate adequate contractility in response to electric field stimulation, indicating the presence of muscle function. These results indicate that a composite tissue consisting of rigid cartilage and/or bone and elastic functional muscle can be bioengineered and can be used for limb replacement.

For in vivo studies, the digit, composed of muscle, bone and tendon, can be engineered in situ in a rabbit model for the restoration of a missing limb.

Example 23

Creating an Intelligent Scaffold

Optimization of digit growth will include the development of new, "intelligent" biomaterial scaffolds that possess the necessary ultrastructural, biomechanical and biological characteristics required for cell attachment, survival, neovascularization, innervation, and tissue maturation in an environment with limited blood supply (i.e. the finger). To engineer a large functional limb tissue in situ, adequate vascularization and innervation are essential.

This example describes the creation of "intelligent" scaffolds that recruit progenitor cells and facilitate the formation of vascular support and innervation via controlled release of growth factors. The intelligent scaffolds accelerate morphogenesis, tissue formation, maturation and function in extensively damaged limbs, to restore digit or limb function to the injured subject.

Figure 10A:
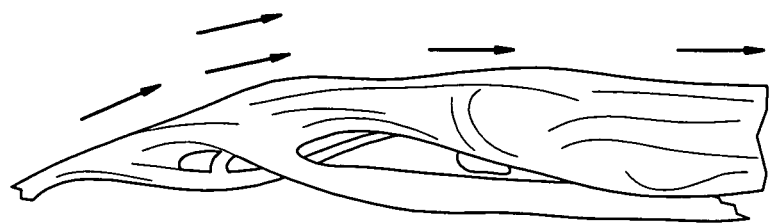
FIG. 10A is a schematic showing that a functional limb requires support and locomotion.
Figure 10B:
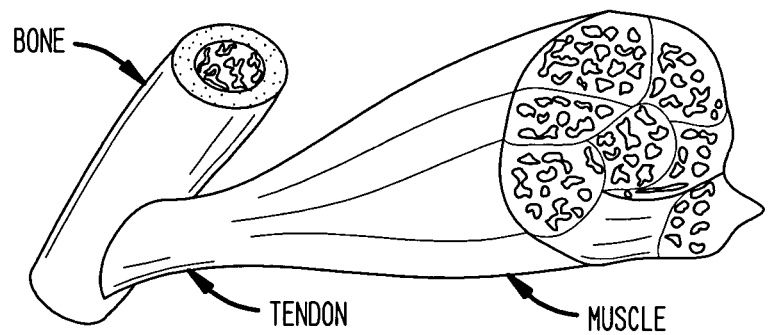
FIG. 10B is a schematic of a composite scaffold system.
Figure 10C:
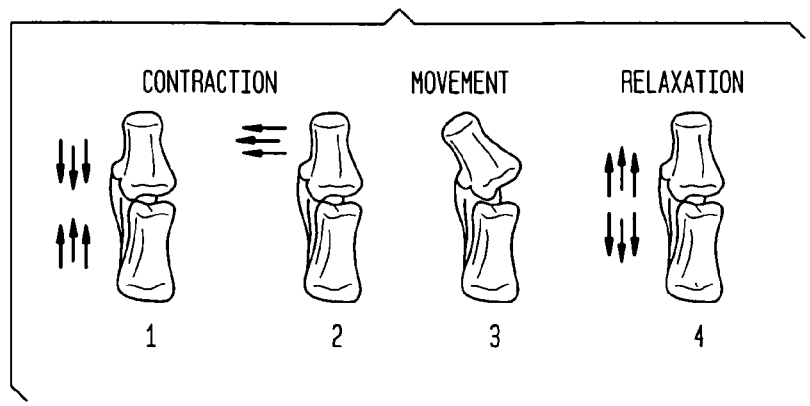
FIG. 10C is a schematic of the artificial composite tissue construct of the invention permitting coordinated motion.

To engineer a functioning limb that would provide structural support and locomotion (FIG. 10A), a composite scaffold system that accommodates each cell type is essential (FIG. 10B). Scaffolds that deliver different cell types have been created that allow a multiple range of motor function in order to demonstrate the feasibility of engineering a functioning limb (FIG. 10C), which shows contraction, movement (bending, flexing) and relaxation. In the ex situ rodent study, polyglycolic acid (PGA) scaffolds were used to configure the rigid portion of the digit, seeded with either cartilage or bone cells, and a collagen based matrix derived from porcine bladders to allow movement by seeding with muscle cells. The PGA scaffolds were composed of 2 cylindrical rods connected to strips of collagen matrix fibers. This configuration allowed for contraction, relaxation and movement of the composite engineered digit-like structure A similar approach was used to mimic native digit structure. Bone scaffolds will be fabricated with pulverized collagen mixed with poly(D,L-lactide-co-glycolide) (PLGA) to achieve improved mechanical and biocompatible properties. Such scaffolds have been fabricated and possess the necessary structural morphology and surface chemistry for cell attachment and growth. Bone scaffolds can be tested for hydrophilicity, mechanical properties, cell viability, as well as cell adhesion and growth.

For tendon and muscle scaffold fabrication, bladder-derived collagen fiber strips will be weaved and anchored to the bone scaffolds. These biomaterials have adequate biomechanical, functional and biocompatibility properties. The properties of each component of the digit scaffolds will be further refined and optimized to achieve adequate structural and biomechanical properties for in situ implantation in the distal limb of the rabbit. Tests involving cell adhesion, proliferation and differentiation will be performed. Physical characteristics, including the hydrophilicity, porosity, degradability, and mechanical properties, of each component of the composite scaffolds will be determined.

Example 24

To Examine the Use of Intelligent Scaffolds with Larger Limbs

Figure 11:
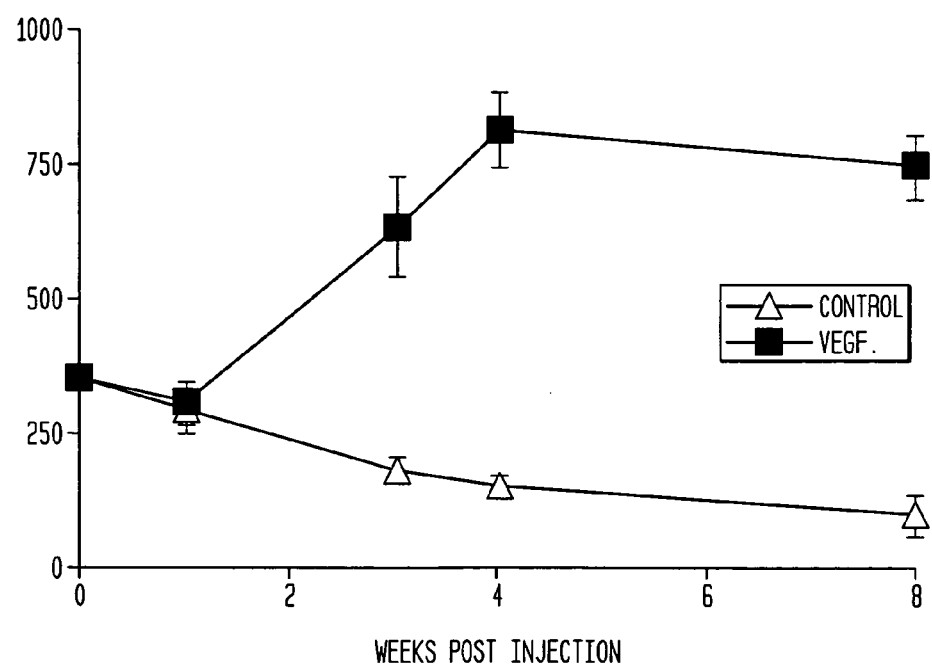
FIG. 11 is a graph showing that nerve growth factor increased the number of regenerated axons compared to the controls without nerve growth factors.
Figure 12:
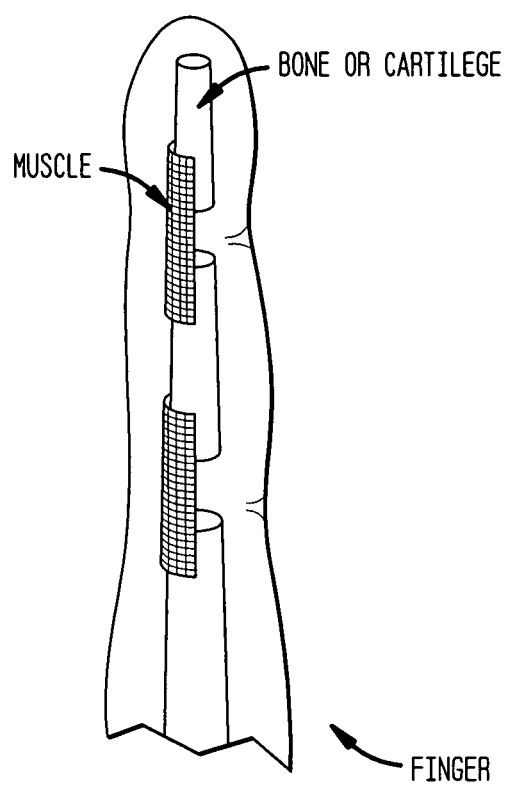
FIG. 12 is a schematic of an artificial finger.

The incorporation of vascular endothelial growth factor VEGF in the engineered muscle significantly enhanced vascularization and muscle tissue mass in vivo. Another critical component involved in the restoration of functional limb tissue is neuronal innervation. Nerve growth factor (NGF) is a potent axonal guiding mediator that promotes reinnervation of tissues. It has been demonstrated that axonal regeneration is significantly accelerated in the NGF contained scaffold, as compared to controls without NGF (FIG. 11). To assess the functionality of the intelligent scaffold, scaffolds will be seeded with rabbit myoblasts and bone cells, and this construct implanted subcutaneously in athymic mice. The engineered muscle tissue will be retrieved at different time points for analysis. Neovascularization will be evaluated by specific EC staining (CD31) and calculating vessel number and distribution. Innervation will be evaluated by specific nerve and acetylcholine receptor expression markers and counting the number of axonal processes and nerve endings using techniques described by Yiou, et al. (2003) *Transplantation;* 76: 1053-60. To develop an intelligent scaffold system that would release active growth factors for an extended period in a controlled manner, technology involving drug delivery system (DDS) is necessary (Rafiti, et al. (1997) *J Control Release;* 43:89-102). VEGF and NGF will be incorporated into the composite digit scaffolds using in situ impregnation and microencapsulation methods. Growth factors will be loaded into individual microspheres using water-in-oil-in-water (W/O/W) emulsion techniques.

In vitro release kinetics will be determined using enzyme-linked immunosorbent assay (ELISA). Biological activities of the growth factors will be evaluated by cell (endothelial and nerve) proliferation assays. In vivo pharmacokinetic studies of the growth factors contained intelligent scaffolds will be performed in athymic mice. Degradation and local tissue response caused by the scaffolds will be tested.

Example 25

In Situ Implantation of a Digit Composed of Bone, Muscle and Tendon, in Rabbits

To determine the feasibility of replacing a missing limb, the regeneration of digit segments with an interconnecting joint of an animal finger (phalanxes) can be performed. Interconnected-composite tissues can be engineered ex situ in the subcutaneous space of mice. To test for in situ implantation, two interconnecting phalanxes of a rabbit digit will be replaced using composite digit tissues composed of bone, muscle and tendon. Due to the limited tissue compartment and blood supply in this area compared with the subcutaneous space of mice, the growth and function of the composite tissue will be monitored.

The existing phalanxes will be excised and the engineered digit segments of the same length and caliber will be interposed and anastomosed. The engineered digit will be evaluated in vivo prior to sacrifice at pre-determined time points. Achievement of digit function is the prime goal of limb restoration. To accurately assess the implanted engineered tissue, in vivo structural and functional assessment will be necessary. Radiography, electromyography (sensory and motor function), physical examination (degree of mobility, extensor and flexor function) and mechanical testing (resistive, compressive and tensile force) will be performed.

To demonstrate that the restored digit tissue can be used for a limb replacement, the retrieved digits will be assessed by structural, mechanical and physiological testing. Mechanical testing will be performed on the bone, tendon, muscle, tendon-bone interface and tendon-muscle interface of the explanted digit using a mechanical tester (Instron). The degree of resistive force in response to compression, compression-relaxation, tension and a multi-directional bending will be tested to determine the levels of tissue maturation. The engineered skeletal muscle tissue will be detached from the bone for muscle functional evaluation. The engineered muscle will be activated using both receptor (i.e., nicotinic acetylcholine receptor) and nonreceptor-mediated (i.e., KCl depolarization) stimulation, as well as electrical field stimulation, using standard physiologic organ bath techniques. Statistical and computer analyses will be used to rigorously evaluate the physiological characteristics of the retrieved segment. A variety of measures, including the rate, magnitude and duration of contractile and relaxation responses, as well as the electrophysiological characteristics of the muscle will be used. In all cases, the retrieved skeletal muscle segments will be compared to the "native" tissue on the contralateral side. Tissue morphology, composition and organization will be assessed by scanning electron microscopy, histo- and immunohistochemistry and molecular analysis.

Example 26

Accelerated Tissue Organization and Maturation of Skeletal Muscle Using a Pre-Conditioning Bioreactor System Muscle tissue organization and maturation is important in achieving muscle tissue function in vivo. Bioreactor studies will be used to determine the optimal conditions for enhancing unidirectional fiber orientation and accelerating muscle tissue maturation. This must be accomplished prior to implanting the muscle tissue in the rabbit with the other composite tissues (i.e., bone and tendon) so as to permit the in vivo environment to complete the maturation process toward fully functional muscle. To achieve this goal, scaffolds seeded with muscle cells will be placed in a bioreactor, and intermittent sinusoidal loading will be employed to provide the muscle with mechanical stimulus.

To this end, myoblasts will be expanded and seeded on muscle scaffolds for pre-conditioning in our bioreactor. The cell containing scaffolds will be cycled at 10-25% of their initial length incrementally over the course of the incubation period. The cycling rate will also be increased incrementally during the course of the bioreactor studies. Initial parameters for stretch and cycling rate will be selected with guidance from previous work in the field. (See e.g., Powell, et al. (2002) *Am J Physiol Cell Physiol;* 283:C1557-65; and Vandenburgh (2002) *Ann NY Acad Sci;* 961:201-2). However, determination of the optimal parameters for stretch and cycling rate will depend on the experimental results, and will be selected based on the configuration that produces the most compatible physiological characteristics.

Example 27

To Demonstrate that an Entire Digit can be Engineered In Situ for Functional Limb Restoration and Engineering of Multiple Digit Segments and In Situ Implantation in a Rabbit Model A larger engineered limb tissue for replacement can be created. A tissue that contains all the necessary tissue elements required to restore a limb, that is bone, muscle and tendon can be created as described above. To achieve a larger sized tissue, the improved intelligent scaffold and tissue maturation system will be used that would permit the enhanced functional tissue formation and maturation. A scaffold system that is capable of delivering angiogenic and neurogenic factors in a controlled manner will be fabricated and configured to serve as a multiple jointed digit construct. Bone marrow-derived bone cells will be seeded on the bone scaffold and in vitro engineered organized muscle tissue will be attached to the scaffold.

The multiple jointed intelligent scaffolds containing the bone and muscle cells will be tested in rabbits through an in situ implantation. The entire digit phalanxes will be excised from the rabbit and the engineered digit segments of the same length and caliber will be interposed and anastomosed. The engineered digit segments will be evaluated in vivo prior to sacrifice at pre-determined time points.

The evaluation of the restored digit tissue will be performed in vivo using radiological analysis to determine bone formation, electromyography to determine muscle function and mechanical testing to determine tissue strength. Radiographic evaluation will be performed to determine the levels of bone, tendon and muscle formation, and electromyography will be performed to demonstrate the degrees of motor and sensory innervation and contractile response of muscle tissue in situ. Physical examination will be performed to test joint and digit mobility, extensor and flexor function. Mechanical testing will also be performed to determine the resistive, compressive and tensile forces of the engineered tissue in vivo.

Structural, biomechanical and physiological testing of the retrieved multiple digit segments will also be performed. Structural morphology will be assessed grossly (quantitatively) and by bone densitometry. The engineered bone mineral content will be assessed, as well as initial and final dimensions of the muscular and tendinous components. In addition to the biomechanical testing methods described above, biomechanical testing of the joint will include bending and stiffness of the joint as measured in three-point bending, and joint dislocation strength measured by failure in tension. Tissue morphology, composition and organization will be assessed by scanning electron microscopy, histo- and immunohistochemistry and molecular analysis.

Example 28

Making and Using the Novel Composite Scaffolding System Comprising a Biodegradable Synthetic Polymer and Naturally Derived Collagen Matrix This example demonstrates the successful fabrication of a bio-hybrid bone scaffold composed of a biodegradable synthetic polymer and a naturally derived collagen matrix that possess necessary characteristics for bone tissue regeneration. In this example, BSM is used as the naturally derived collagen matrix and PLGA is used as the biodegradable synthetic polymer. The BSM-PLGA composite scaffolds are hydrophilic and possess porous structures with a consistent interconnectivity throughout the entire scaffold which resulted in uniform cell seeding, adhesion and proliferation. The BSM-PLGA composite scaffolds are non-toxic, easily fabricated and provide structural features that enhance the formation of bone tissue for therapeutic regeneration.

Creation of bone tissue using cells requires a scaffold that serves as a cell carrier which would provide structural support until bone tissue forms in vivo. The scaffold for bone tissue engineering should be biocompatible and possess mechanical stability, a controlled degradation rate, hydrophilic surface chemistry and an appropriate porosity for cell accommodation. In this invention, a composite scaffold for bone regeneration is disclosed that meets these criteria by hybridizing BSM as a natural bioactive material with synthetic PLGA polymers. This example demonstrates that the BSM-PLGA composite scaffolds are non-toxic, easily fabricated, and provide structural support with abundant pores with good interconnectivity.

BSM was selected for its biocompatibility, hydrophilic nature and ability to induce cell proliferation. BSM consists mainly of type I and type III collagen, elastin fibers and various proteins such as fibronectin and vitronectin that contain the arginine-glycine-aspartate (RGD) peptide binding motif. The presence of these extracellular proteins may enhance cell adhesion, survival and proliferation. However, BSM alone is well suited for bone graft applications due to its small pore size, poor interconnectivity and inability to maintain structural integrity. To overcome these limitations, a natural-synthetic hybrid scaffold was designed that would possess an interconnected network of pores and sufficient mechanical and physicochemical properties that would maintain structural integrity, thus preventing collapse during the handling and implantation process. The microarchitecture of the composite scaffolds did not differ from the control PLGA scaffold, indicating that the incorporation of BSM did not alter structural changes during the fabrication process. Further, the composite scaffolds provided desirable surface properties necessary for cell attachment and proliferation.

The surface properties of biomaterials play a major role in cellular interaction, such as cell adhesion, infiltration and proliferation. The surface characteristics of many synthetic polymers including the PLGA are hydrophobic, which unfavorably influence their biocompatibility during the initial stage of contact with the biological environment. As shown below, a hydrophilic surface was successfully achieved without compromising the structural properties of the scaffold by introducing the BSM component in the composite scaffold. The hydrophilicity of the BSM-PLGA composite scaffold was found to rely strongly on the content of BSM, which mainly possesses hydrophilic proteins such as collagen and elastin. Therefore, enhanced penetration of culture medium, enhanced cell seeding and uniform distribution and accelerated cell migration were achieved.

A scaffold material for bone regeneration should be biocompatible and safe for implantation. Cellular interactions of the BSM-PLGA composite scaffold were tested by using the two widely accepted complementary assays; cell viability and mitochondrial metabolic activity. The cell viability assay using Neutral Red, which is based on dye incorporation into lysosomes, and the MTT assay, which is based on the intact activity of a mitochondrial enzyme, demonstrated that the BSM-PLGA composite scaffolds are safe for the cells tested.

In this example, the composite scaffolds was tested with two different cell types that could be used in orthopedic applications. Primary mature osteoblasts and stem cells form bone tissues when implanted in vivo or differentiated into bone cells. These cell types were used to determine their ability to survive, adhere and proliferate on the composite scaffolds. Cell accommodation, adhesion and proliferation were approximately 80% higher in the BSM-PLGA composite scaffolds, as compared to the control scaffolds using these two cell types. Fabrication of the scaffolds with an appropriate pore size, porosity and surface hydrophilicity resulted in abundant cell accommodation with increased cell proliferation. The incorporation of BSM significantly improved the biological activities of the scaffold, while maintaining physical and structural stability.

1. Materials and Methods

A. Materials

Porcine bladders, obtained from donor animals, were decellularized using a multiple step process (De Filippo R E, Yoo J J, Atala A. *J Urol* 2002; 168:1789-92). Briefly, the bladders were rinsed thoroughly with phosphate-buffered saline (PBS). The bladder submucosa was microdissected and isolated from the muscular and serosal layers. Under continuous agitation, the bladder submucosa was rinsed with deionized water for 24 hr and placed in a solution containing 0.2% Triton X-100 and 0.03% ammonium hydroxide for 14 days to remove all cellular components. The bladder submucosa was washed with deionized water containing 10% cefazolin (APOTHECON, G. C. Hanford Mfg. Co., Syracuse, N.Y., USA) for an additional 24 hr. The BSM was freeze-dried at −50° C. for 48 hr using a lyophilizer (FreeZone 12, Model 775410, LABCONCO, Kansas City, Mo., USA), followed by pulverization in a freezer mill (SPEX 6700, Mutchen, USA) at −198° C.

Poly(D,L-lactide-co-glycolide) (PLGA, 110,000 g/mole, 50:50 by mole ratio of lactide to glycolide, Resomer RG506) was obtained from Boehringer Ingelheim (Ingelheim, Germany). Collagraft, collagen-calcium phosphate ceramic graft material, was purchased from Zimmer (Warsaw, Ind., USA). All chemicals were obtained from Sigma Co. (St Louis, Mo., USA) and used as received unless it is stated otherwise.

B. Methods (1). Preparation of BSM-PLGA Composite Scaffold and PLGA Scaffold

The BSM-PLGA composite scaffold was fabricated using a solvent casting/particulate leaching process from mixtures of PLGA and BSM powder. To obtain the desired structural configuration and surface properties of the scaffold, fabrication parameters such as composition ratios of PLGA to BSM and porogen were controlled. As a porogen, sodium chloride (NaCl) crystals were sieved to obtain a size range of 300 to 500 µm to target a pore size range of 100~250 µm, which is ideal for tissue engineering applications. The particles were added to 20 wt/vol % PLGA in methylene chloride and BSM powder and thoroughly mixed using a vortex. PLGA and BSM powder were mixed with equal proportion by weight. The weight ratio of PLGA and BSM to NaCl was 1:10. This formulation was determined by previous experiments that achieved the best structural integrity for a bone scaffold. The BSM-PLGA composite scaffold containing NaCl was air-dried for 24 hr and vacuum-dried (5~10 mbar) for 48 hr to remove residual solvent. The scaffolds were immersed in deionized water for 48 hr with water change every 6 hr to remove the embedded salt. The scaffolds were lyophilized and stored in a desiccator until use. PLGA scaffolds without BSM were used as a control, and were fabricated using the same method as the BSM-PLGA composite scaffold preparation (1:10).

(2). Scaffold Characterization

Surface and cross-sectional morphology of all scaffolds was examined by scanning electron microscopy (SEM; Model S-2260N, Hitachi Co. Ltd., Japan). Samples were observed under an environmental SEM (Backscatter electron (BSE) mode) without any conductive coating. The average pore size and porosity of the composite scaffolds were analyzed by a mercury intrusion porosimeter (AutoPore IV 9500, Micromeritics Co. Ltd., Norcross, Ga., USA). The porosimeter was set at a solid penometer volume of 6.7~7.3 mL, and a mercury filling pressure of 3.4 KPa and intruded to a maximum pressure of 414 MPa. Individual samples of 0.1 g were analyzed.

A fluid uptake test was used to determine the hydrophilicity of the composite scaffold. For the evaluation of fluid uptake capacity, the composite scaffold was immersed in PBS at pH 7.4 for 30 sec. Percent fluid uptake was calculated according to the following equation:

$$\text{Fluid uptake (\%)} = (W_s - W_o)/W_o \times 100$$

where $W_o$ is the dry sample and $W_s$ is the wet sample.

(3). Mechanical Testing

Mechanical properties were assessed on the cylinder-shaped BSM-PLGA composite scaffolds (5 mm of thickness×10 mm of diameter) using a mechanical tester with a compression interface diameter of 2 inches (Instron Model 5544, Canton, Mass., USA). A two kN load cell at a crosshead speed of 0.4 mm/min was used for compression testing. The testing was performed under both dry and wet conditions. The compressive strength was determined from the maximum load recorded. Young's modulus was calculated from the slope of the initial linear segment of the stress-strain curve at maximum stress. At least four specimens were tested for each scaffold, and the average and the standard deviation were calculated.

(4). Biological Activity Testing i. Cell Culture

Two different types of cells were used in this study, embryonic stem (ES) cells, which are capable of becoming bone cells, and primary bovine osteoblasts (bOBs). Human ES cells (hES H7) (Thomson J A et al. *Science* 1998; 282:1145-7) were maintained on mitomycin C-treated mouse embryonic fibroblasts (MEF, feeder layer) in a growth medium: Knockout high glucose DMEM supplemented with 500 U/mL penicillin, 500 µg/ml streptomycin, 2 mM GlutaMAX I, 1% non-essential amino acid solution, 0.1 mM β-mercaptoethanol, 4 ng/mL bFGF, 1 ng/mL human LIF (Chemicon, Temecula, Calif.), 8% Serum Replacement (SR) and 8% Plasmanate (Bayer). To induce the formation of embryoid bodies (EBs), hES cells were trypsinized and approximately $1 \times 10^7$ hES cells transferred to a 100 mm Petri dish. Embryoid bodies were grown in the same culture medium as hES cells without LIF, Plasmanate and bFGF. The EBs were cultured for 5 days and dissociated with trypsin and plated on culture dishes. All reagents for cell culture were purchased from Invitrogen Co. (Gibco Cell Culture, Carlsbad, Calif., USA).

Bovine OBs were isolated from the periosteum of calf forelimb. The periosteum was harvested from fresh tissue and cut into 1 cm² pieces under aseptic conditions. The periosteum fragments were placed on 100 mm tissue culture dishes with culture medium (Medium 199 supplemented with 10% fetal calf serum (FCS), 50 mg ascorbic acid, 100 U/mL Penicillin and 100 µg/mL Streptomycin). The medium was changed every 3 days until a confluent monolayer of cells was formed. The periosteal tissue was removed and the bOBs were subcultured with 0.05% trypsin-EDTA and further expanded.

ii. Cytotoxicity Assessment

Scaffolds 3×3×2 mm in size were placed at the center of subconfluent hEBs and bOBs on 96-well plates. Latex fragments of equal size served as a positive control, and cells with media only served as a negative control. The cell-material contact was maintained for 7 days at 37° C. in 5% $CO_2$ and, culture medium was changed every 3 days. After 7 days, scaffolds were removed and the culture tested for cell viability using Neutral Red and mitochondrial metabolic activity by 3-(4,5-dimethylthiazol-2-yl)-2,5-diphenyl tetrazolium bromide (MTT) assay (Pariente J L, Kim B S, Atala A. *J Biomed Mater Res* 2001; 55:33-9).

For the cell viability assay, cells were rinsed with 1×PBS and 0.005 wt/vol % Neutral Red in culture medium was added to each well. After 4 hr of incubation at 37° C., the Neutral Red solution was removed and dye extraction was performed by adding 1% acetic acid in 50% ethanol solution per well. Absorbance was measured using a microplate reader ($EL_X$ 800, Bio-Tex Instruments Inc., Winooski, Vt., USA) at 540 nm. The intensity of red color obtained was directly proportional to the viability of cell populations and inversely proportional to the cytotoxicity of the scaffolds.

For the mitochondrial metabolic activity, cells were rinsed with 1×PBS and 1.0 mg/mL of MTT in PBS containing 1.0 g/L glucose was added to the wells. After 4 hr of incubation at 37° C., the MTT solution was removed and insoluble formazan crystals were dissolved in dimethyl sulfoxide (DMSO). Absorbance was measured at 540 nm using a microplate reader. The intensity of blue color obtained was directly proportional to the metabolic activity of the cell populations and inversely proportional to the cytotoxicity of the scaffolds.

iii. Cell Adhesion and Proliferation

Biological activity of the BSM-PLGA composite scaffolds was determined by testing the ability of cells to adhere and proliferate. To assess these characteristics, both hEBs and bOBs were seeded onto separate composite scaffolds. Briefly, all scaffolds were pre-conditioned and sterilized with 70% ethanol for 30 min and rinsed with 1×PBS five times. Scaffolds (8×8×3 mm³) were placed in each well of a 96-well culture plate. 40 µL of cell suspension ($1 \times 10^6$ cells/mL) was seeded on each scaffold. To observe cell morphology, the cell-scaffold constructs were fixed with 2.5% glutaraldehyde solution. The constructs were dehydrated through a series of graded ethanol solutions, followed by observation with SEM.

Mitochondrial dehydrogenase activity of the cells on scaffolds was determined by MTT assay after 1, 2, 4 and 8 days of culture. In brief, 50 µL of 1 mg/mL MTT solution was added to each well containing fresh medium and incubated at 37° C. and 5% $CO_2$ for 4 hr. The formazan-formed scaffolds were imaged using a digital camera to assess cellular distribution. The intracellular formazan accumulated in the cytoplasm of viable cells was solubilized using DMSO. Absorbance was measured at 540 nm using a microplate reader. Cell proliferation was assessed by the intensity of blue color obtained, which was directly proportional to the metabolic activity of the cell population. The optical density was recorded for quantification (n=5) of adhered cells within the scaffolds. Cell adhesion was further confirmed by scanning electron microscopy of the cell seeded scaffolds.

iv. Statistical Analysis

The differences between the composite scaffolds and controls in fluid uptake ability, average pore size, porosity, cell viability and mitochondrial metabolic activity were evaluated by Student's t-test. Data from the cell proliferation assay were analyzed by ANOVA. Differences were considered significant at $P<0.05$.

2. Fabrication and Characterization of the BSM-PLGA Composite Scaffolds

Figure 13A:
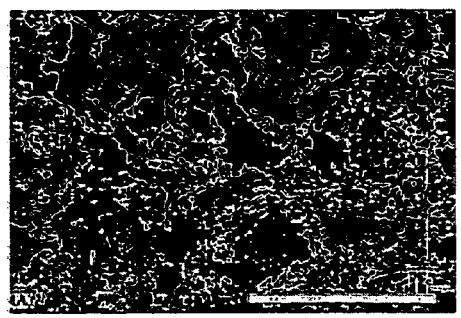
FIG. 13A is a scanning electron microscope (SEM) cross-sectional observation of the BSM-PLGA composite scaffold of the present invention.
Figure 13B:
FIG. 13B is an SEM cross-sectional observation of PLGA scaffold.
Figure 13C:
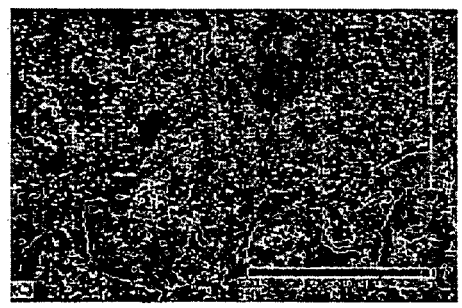
FIG. 13C is an SEM cross-sectional observation of Collagraft scaffold.

The BSM-PLGA composite scaffolds, fabricated by the solvent casting/particulate leaching process, exhibited highly porous and uniform interconnected structures. BSM particles with a size ranging from 6~32 μm were homogeneously embedded in the composite scaffolds as demonstrated by SEM (FIG. 13). FIG. 13 is a cross-sectional observation of (A) the BSM-PLGA composite scaffold, (B) PLGA scaffold and (C) Collagrafts. The BSM-PLGA composite scaffold and PLGA scaffold show similar architecture and possess uniform porous structures with a consistent interconnectivity throughout the entire scaffold. However, Collagrafts shows small pores and minimal interconnectivity. Scale bar indicates 500 mm (SEM, original magnification: ×100).

There were distinct morphological differences between the BSM-PLGA composite scaffold and Collagraft, while the BSM-PLGA composite scaffold and PLGA scaffold were similar in microstructure (FIG. 13), pore size and porosity (Table 1). The exterior surface, serial cross-section and side wall morphologies of the BSM-PLGA composite scaffolds and PLGA scaffolds exhibited a highly porous structure with interconnectivity that would support adequate cell seeding, adhesion and proliferation. The average pore size of the BSM-PLGA composite scaffolds was 121.84±23.44 μm (Table 1). The average pore size and porosity of the BSM-PLGA composite scaffolds were significantly different compared to Collagraft ($P<0.05$). The BSM-PLGA composite scaffold exhibited uniformly distributed-interconnecting pores in its inner microstructures which were successfully achieved by a particulate leaching process.

The fluid uptake ability of the BSM-PLGA composite scaffolds was superior when compared with PLGA scaffold and Collagraft ($P<0.01$). The fluid uptake ability of BSM-PLGA composite scaffolds increased with the elevation of the BSM to PLGA ratio due to the hydrophilic characteristics of the BSM (data not shown).

Compressive strengths of the BSM-PLGA composite and PLGA scaffolds were significantly higher than that of Collagraft in dry condition (Table 1). Under dry condition, the mechanical properties of the composite scaffold were similar to PLGA scaffold. On the contrary, the composite scaffold showed increased Young's modulus and decreased compressive strengths under wet condition due to the water-uptake in BSM. There were statistical differences between dry and wet conditions ($P<0.05$) in both the BSM-PLGA composite scaffold and Collagraft.

3. Biological Activity Testing (1). Cytotoxicity Assessment

Figure 14A:
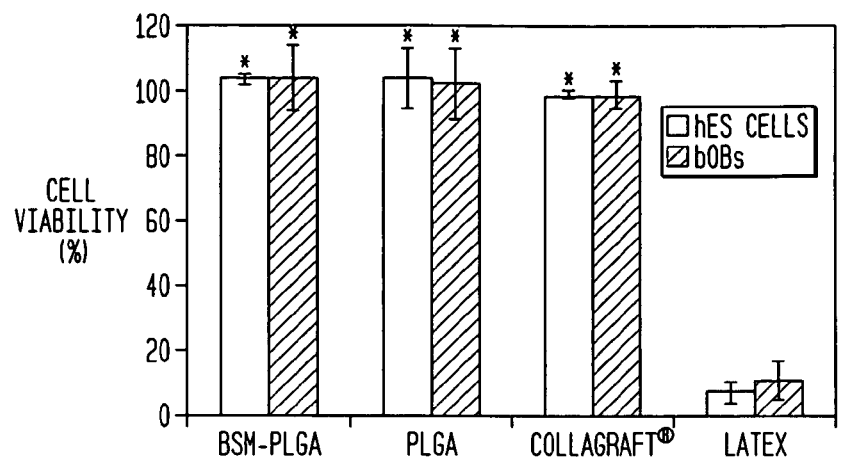
FIG. 14A is a bar graph showing similar cell survival of human embryonic stem cells (hES) cells and bovine osteocytes (bOBs) cultured on various bone scaffolds at 7 days as measured by neutral red assay.
Figure 14B:
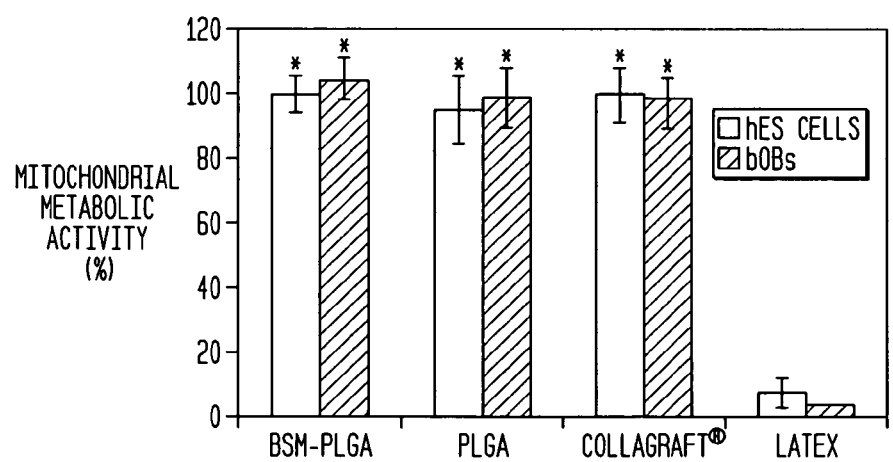
FIG. 14B is a bar graph showing similar mitochondrial metabolic activity of hES cells and bOBs cultured on various bone scaffolds at 7 days as measured by MTT assay.

Cytotoxicity assay using Neutral Red indicated that the BSM-PLGA composite scaffold, PLGA scaffold and Collagraft did not demonstrate significant differences in cell viability, when compared to cells grown on tissue culture plates as a negative control (FIG. 14A). Meanwhile, the latex used as a positive control, showed a cell viability of 7.3% of dissociated cells from hEBs and 10.5% of bOBs when compared to the negative control, indicating a high cytotoxicity. The mitochondrial metabolic activity of the BSM-PLGA composite scaffold, PLGA scaffold and Collagraft was also determined by the MTT assay using the direct contact method (FIG. 14B). Direct contact with latex significantly decreased mitochondrial activity by 92.1% in hEBs cultures and 96% in bOBs cultures after 7 days. FIG. 14 shows the viability (A) and mitochondrial metabolic activity (B) of hES cells and bOBs cultured on bone scaffolds show similar cell survival in all experimental scaffolds at 7 days by neutral red assay (A) and MTT assay (B). $P<0.01$ compared to Latex (positive control).

(2) Cell Adhesion and Proliferation

Figure 15:
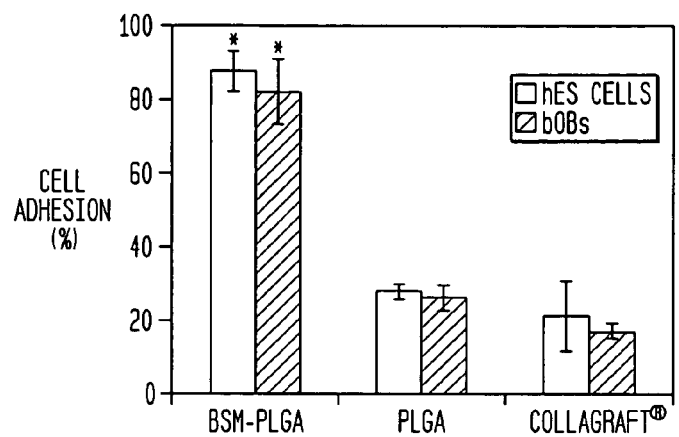
FIG. 15 is a bar graph comparing the percent cell adhesion on various scaffolds with hES and bOSs cells.

Cross-sectional SEM images of the BSM-PLGA composite scaffold, PLGA scaffold and Collagraft 1 day after seeding with hEBs and bOBs were taken (data not shown). After 1 day of culture, the cell-seeded BSM-PLGA scaffold showed a homogeneous cell distribution. The PLGA scaffold and Collagraft showed a sparse cell distribution. Cell adhesion to the scaffold was quantified as shown in FIG. 15. There was a significant difference ($P<0.01$) between the BSM-PLGA composite scaffold and the others. A similar observation was achieved with bOBs cells (data not shown). In the BSM-PLGA composite scaffold, the seeded cells were uniformly distributed and adhered to the walls of the pores. However, there were only a few cells found in the pores of the PLGA

TABLE 1

Physical Properties of the BSM-PLGA Composite Scaffold, PLGA Scaffold, and Collagraft.

| Samples | Average pore size (μm) | Porosity (%) | Compression strength (MPa) | Young's modulus (MPa) |
| --- | --- | --- | --- | --- |
| BSM-PLGA | 121.84 ± 23.44* | 94.79 ± 10.76* | 0.83 ± 0.05(d)* | 5.56 ± 0.64(d)* |
|  |  |  | 0.15 ± 0.02(w) | 0.24 ± 0.07(w) |
| PLGA | 134.22 ± 12.56* | 92.43 ± 3.21* | 1.20 ± 0.13(d)* | 8.33 ± 0.23(d)* |
|  |  |  | 1.14 ± 0.07(w)* | 7.69 ± 0.18(w)* |
| Collagraft ® | 26.44 ± 7.98 | 70.69 ± 6.52 | 0.31 ± 0.04(d) | 1.27 ± 0.12(d) |
|  |  |  | 0.12 ± 0.07(w) | 0.11 ± 0.08(w) |

*$p < 0.05$, compared to Collagraft ®.
Dry (d) and wet (w) conditions.

scaffold and Collagraft. At 8 days of culture, both cell types proliferated on the BSM-PLGA composite scaffold, indicating that the scaffold was conducive to cell adhesion and proliferation. A uniform cell distribution was observed throughout the entire BSM-PLGA scaffold. MTT staining of the BSM-PLGA composite scaffold showed the uniform penetration of formazan crystals on the surface and vertical cross-sections, indicating adequate cell adhesion and distribution throughout the inner structure. Cell adhesion on the BSM-PLGA composite scaffold was significantly higher than on PLGA scaffold and Collagraft (FIG. 15). The percentage of the seeded hEBs and bOBs adhered to the BSM-PLGA composite scaffold was 87.70±5.46% and 82.23±8.77% of the initial cell number, respectively. The levels of cell adhesion showed a significant difference (P<0.01) between the BSM-PLGA composite scaffold and Collagraft.

Figure 16:
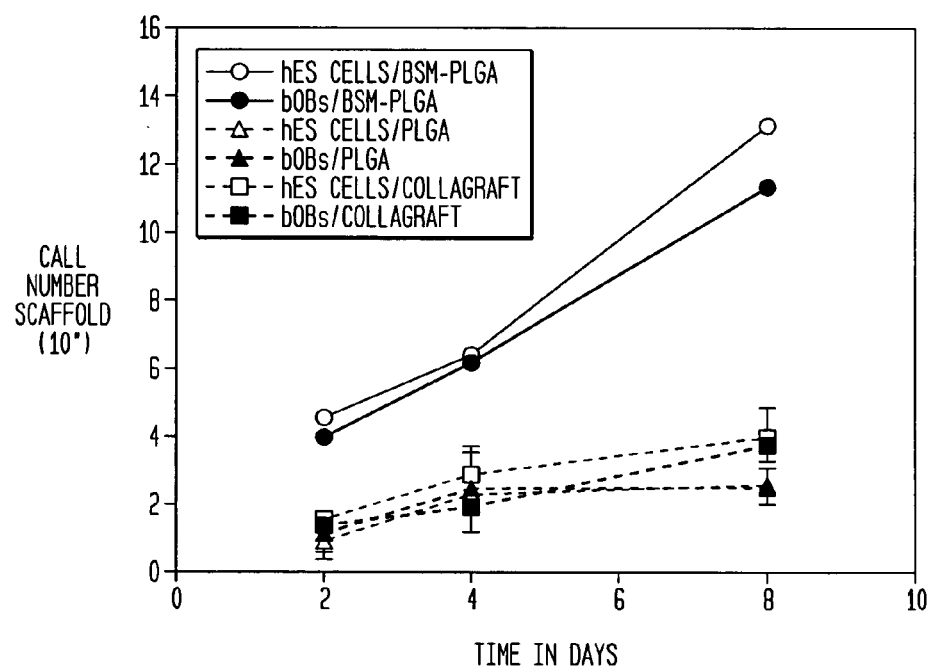
FIG. 16 is a graph comparing cell proliferation of the BSM-PLGA composite scaffold, PLGA scaffold and Collagraft up to 8 days culture, as determined by MTT assay.

Both the hEBs and bOBs were cultured on the BSM-PLGA composite scaffold, PLGA scaffold and Collagraft for up to 8 days. The rate of the cell proliferation on the BSM-PLGA composite scaffold was significantly higher than that of the PLGA scaffold and Collagraft (P<0.05) (FIG. 16), and did not show significant differences between the cell types at different culture time points. FIG. 16 shows cell proliferation of the BSM-PLGA composite scaffold, PLGA scaffold and Collagrafts up to 8 days culture, as determined by MTT assay. The cells seeded on BSM-PLGA composite scaffolds show a higher proliferation rate when compared to the other experimental scaffolds (P<0.05). Cells proliferated gradually in the BSM-PLGA composite scaffold, PLGA scaffold and Collagrafts for 8 days of culture. The initial number of seeded cells was $4 \times 10^4$ cells/scaffold.

This example demonstrates the successful fabrication of a bio-hybrid bone scaffold composed of BSM and PLGA that possess necessary characteristics for bone tissue regeneration. The BSM-PLGA composite scaffolds are hydrophilic and possess porous structures with a consistent interconnectivity throughout the entire scaffold which resulted in uniform cell seeding, adhesion and proliferation. The BSM-PLGA composite scaffolds are non-toxic, easily fabricated and provide structural features that may enhance the formation of bone tissue for therapeutic regeneration.

The invention claimed is:

1. A method of producing an artificial composite flexible digit construct permitting coordinated motion, comprising:
   providing a first biocompatible, biodegradable matrix, wherein the first matrix comprises a composite synthetic polymer and collagen matrix having a substantially uniform porous structure and a porosity greater than about 50% for cell accommodation, the composite further comprising about 25% to about 75% synthetic polymer to provide sufficient rigidity to provide structural support for bone tissue regeneration;
   seeding the first matrix with an isolated population of cells selected from the group consisting of cartilage-forming cells, bone-forming cells and combinations thereof;
   providing a second biocompatible matrix, wherein the second matrix comprises a flexible, collagen-containing matrix;
   seeding the second matrix with an isolated population of muscle progenitor cells (MPCs);
   preconditioning the seeded second matrix in a bioreactor that provides intermittent stretching of the MPC-seeded second matrix to promote unidirectional muscle fiber growth and orientation;
   joining the first matrix to the second matrix; and
   joining the second matrix to an additional matrix or a bone structure such that the second matrix produces a flexible linkage therebetween to produce the artificial composite flexible digit construct capable of coordinated motion.

2. The method of claim 1, wherein the second matrix is joined to two separate first matrices.

3. The method of claim 1, wherein the second matrix is joined to the first matrix and a natural bone structure.

4. The method of claim 1, wherein the first matrix is selected from the group consisting of an electrospun substrate, a decellularized substrate, and a synthetic polymer substrate.

5. The method of claim 1, wherein the second matrix is selected from the group consisting of a decellularized bladder submucosa substrate and an electrospun substrate.

6. The method of claim 1, wherein the step of joining the first matrix and the second matrix comprises using a joining technique selected from the group consisting of suturing, heating, and gluing with biological glue.

7. The method of claim 1, wherein the first matrix and the second matrix further comprise a biological agent selected from the group consisting of nutrients, growth factors, cytokines, extracellular matrix components, inducers of differentiation, products of secretion, immunomodulators, proteins, antibodies, nucleic acids molecules, carbohydrates, and biologically-active compounds which enhance or allow growth of the cellular network or nerve fibers.

8. The method of claim 7, wherein the biological agent is a growth factor selected from the group consisting of transforming growth factor-alpha (TGF-α), transforming growth factor-beta (TGF-β), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor.

9. The method of claim 1, wherein the first matrix is selected from the group consisting of a cartilage tissue layer and a bone tissue layer.

10. The method of claim 1, wherein the bone-forming cells are selected from the group consisting of osteogenic cells, osteoblasts, osteocytes, osteoclasts, and bone-lining cells.

11. The method of claim 1, wherein the first matrix is a composite scaffold.

12. A method of producing an artificial composite flexible joint construct permitting coordinated motion, comprising:
   providing a first biocompatible, biodegradable matrix, wherein the first matrix comprises a composite synthetic polymer and collagen matrix having a substantially uniform porous structure and a porosity greater than about 50% for cell accommodation, the composite further comprising about 25% to about 75% synthetic polymer to provide sufficient rigidity to provide structural support for bone tissue regeneration;
   seeding the first matrix with an isolated population of cells selected from the group consisting of cartilage-forming cells, bone-forming cells and combinations thereof;
   providing a second biocompatible matrix, wherein the second matrix comprises a flexible, collagen-containing matrix;
   seeding the second matrix with an isolated population of muscle progenitor cells (MPCs);
   preconditioning the seeded second matrix in a bioreactor that provides intermittent stretching of the MPC-seeded second matrix to promote unidirectional muscle fiber growth and orientation;

joining the first matrix to the second matrix; and
joining the second matrix to an additional matrix or a bone structure, such that the second matrix produces a flexible linkage therebetween to produce the artificial composite flexible joint construct capable of coordinated motion,
wherein at least one of the isolated populations of cells have been transformed to express a biological agent.

13. The method of claim 12, wherein the isolated population of cells expressing the biological agent is transfected with a plasmid encoding the biological agent.

14. The method of claim 12, wherein the biological agent is selected from the group consisting of nutrients, growth factors, cytokines, extracellular matrix components, inducers of differentiation, products of secretion, immunomodulators, proteins, antibodies, nucleic acids molecules, carbohydrates, and biologically-active compounds which enhance or allow growth of the cellular network or nerve fibers.

15. The method of claim 12, wherein the biological agent is a growth factor selected from the group consisting of transforming growth factor-alpha (TGF-α), transforming growth factor-beta (TGF-β), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor.

16. A method of producing an artificial composite flexible joint construct permitting coordinated motion, comprising:
providing a first biocompatible, biodegradable matrix, wherein the first matrix comprises a composite synthetic polymer and collagen matrix having a substantially uniform porous structure and a porosity greater than about 50% for cell accommodation, the composite further comprising about 25% to about 75% synthetic polymer to provide sufficient rigidity to provide structural support for bone tissue regeneration;
seeding the first matrix with an isolated population of osteoblasts and at least one population of cells selected from the group consisting of cartilage cells, chondrocytes and chondroblasts;
providing a second biocompatible matrix, wherein the second matrix comprises a flexible, collagen-containing matrix;
seeding the second matrix with an isolated population of muscle progenitor cells (MPCs);
preconditioning the seeded second matrix in a bioreactor that provides intermittent stretching of the MPC-seeded second matrix to promote unidirectional muscle fiber growth and orientation;
joining the first matrix to the second matrix; and
joining the second matrix to an additional matrix or a bone structure, such that the second matrix produces a flexible linkage therebetween to produce the artificial composite flexible joint construct capable of coordinated motion.

17. The method of claim 16, wherein the first matrix is an electrospun matrix.

18. A method of producing an artificial composite flexible joint construct permitting coordinated motion, comprising:
providing a first biocompatible, biodegradable matrix, wherein the first matrix comprises a composite synthetic polymer and collagen matrix having a substantially uniform porous structure and a porosity greater than about 50% for cell accommodation, the composite further comprising about 25% to about 75% synthetic polymer to provide sufficient rigidity to provide structural support for bone tissue regeneration;
seeding the first matrix with an isolated population of cells selected from the group consisting of cartilage-forming cells, bone-forming cells and combinations thereof;
providing a second biocompatible matrix, wherein the second matrix comprises a flexible, collagen-containing matrix;
seeding the second matrix with an isolated population of muscle progenitor cells (MPCs);
preconditioning the seeded second matrix in a bioreactor that provides intermittent stretching of the MPC-seeded second matrix to promote unidirectional muscle fiber growth and orientation;
joining the first matrix to the second matrix; and
joining the second matrix to an additional matrix or a bone structure, such that the second matrix produces a flexible linkage therebetween to produce the artificial composite flexible joint construct capable of coordinated motion,
wherein at least one of the first and second matrix further comprises at least one nanoparticle coupled to a releasable biological agent and incorporated within the matrix.

19. The method of claim 1, wherein the step of providing the first biocompatible matrix comprises providing a first matrix comprising a composite synthetic polymer and submucosal-derived collagen matrix.

20. The method of claim 12, wherein the step of providing the first biocompatible matrix comprises providing a first matrix comprising a composite synthetic polymer and submucosal-derived collagen matrix.

21. The method of claim 16, wherein the step of providing the first biocompatible matrix comprises providing a first matrix comprising a composite synthetic polymer and submucosal-derived collagen matrix.

22. The method of claim 18, wherein the step of providing the first biocompatible matrix comprises providing a first matrix comprising a composite synthetic polymer and submucosal-derived collagen matrix.

23. The method of claim 1, wherein the additional matrix is selected from the group consisting of an electrospun substrate, a decellularized substrate, and a synthetic polymer substrate.

24. The method of claim 1, wherein the additional matrix is selected from the group consisting of a cartilage tissue layer and a bone tissue layer.

25. The method of claim 12, wherein the additional matrix is selected from the group consisting of an electrospun substrate, a decellularized substrate, and a synthetic polymer substrate.

26. The method of claim 12, wherein the additional matrix is selected from the group consisting of a cartilage tissue layer and a bone tissue layer.

27. The method of claim 16, wherein the additional matrix is selected from the group consisting of an electrospun substrate, a decellularized substrate, and a synthetic polymer substrate.

28. The method of claim 16, wherein the additional matrix is selected from the group consisting of a cartilage tissue layer and a bone tissue layer.

29. The method of claim 18, wherein the additional matrix is selected from the group consisting of an electrospun substrate, a decellularized substrate, and a synthetic polymer substrate.

30. The method of claim 18, wherein the additional matrix is selected from the group consisting of a cartilage tissue layer and a bone tissue layer.

* * * * *